United States Patent [19]

Ramsey et al.

[11] Patent Number: 4,889,991

[45] Date of Patent: Dec. 26, 1989

[54] GAMMA RADIATION DETECTOR WITH ENHANCED SIGNAL TREATMENT

[75] Inventors: Raymond C. Ramsey; Marlin O. Thurston, both of Columbus, Ohio

[73] Assignee: Neoprobe Corporation, Columbus, Ohio

[21] Appl. No.: 248,816

[22] Filed: Sep. 23, 1988

[51] Int. Cl.$^4$ ............................................. G01T 1/161
[52] U.S. Cl. ................................ 250/336.1; 128/659; 250/370.01
[58] Field of Search ........................... 128/659, 654; 250/370.07, 370.01, 336.1

[56] References Cited

U.S. PATENT DOCUMENTS 4,243,884  1/1981  Avera, Jr. .................... 250/361 R
4,782,840  11/1988 Martin, Jr. et al. ................ 128/654
4,801,803  1/1989  Denen et al. ..................... 250/336.1

Primary Examiner—Constantine Hannaher
Attorney, Agent, or Firm—Mueller and Smith

[57] ABSTRACT

A hand-held gamma radiation probe is employed to locate radiation concentrations in animal tissue in conjunction with a control function providing an enhanced audio output particularly suited for cuing the user as to source position. The probe is positioned at a location on the animal body representing background radiation and a squelch low count rate is developed therefrom. The squelch low count rate is multiplied by a range factor to develop a squelch high count rate and frequencies are developed from a look-up frequency table from lowest to highest in correspondence with the developed high and low squelch count rates. Slew rate limiting of the count rates is provided by development of a squelch delta value representing the difference between the squelch high and low count rates divided by a time element. Selection of frequencies for audio output from the frequency table is limited by the value of the squelch delta value. A weighting of received radiation counts is carried out continuously to develop count rate values used by the system.

24 Claims, 12 Drawing Sheets

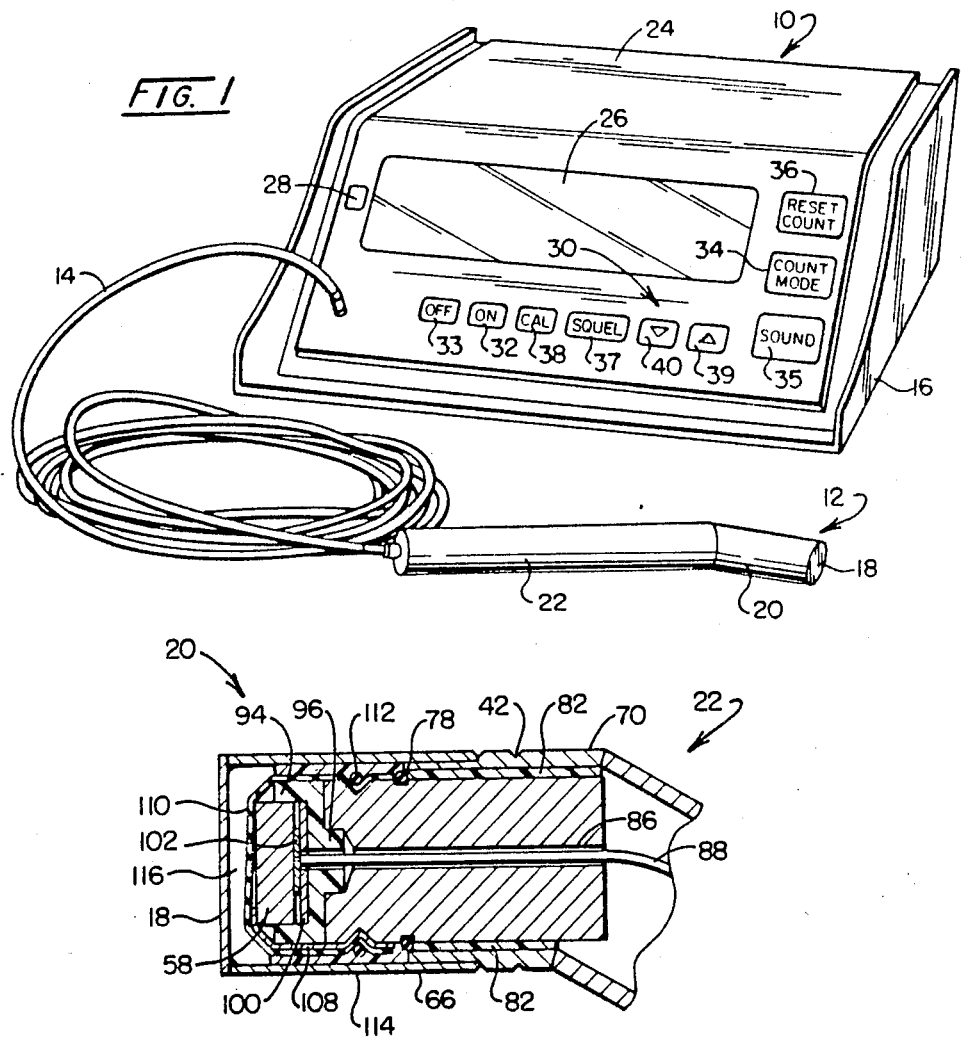

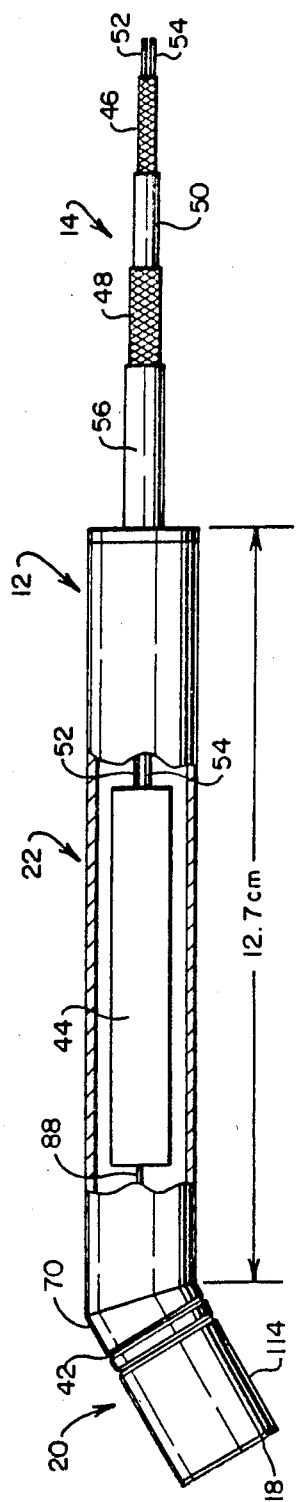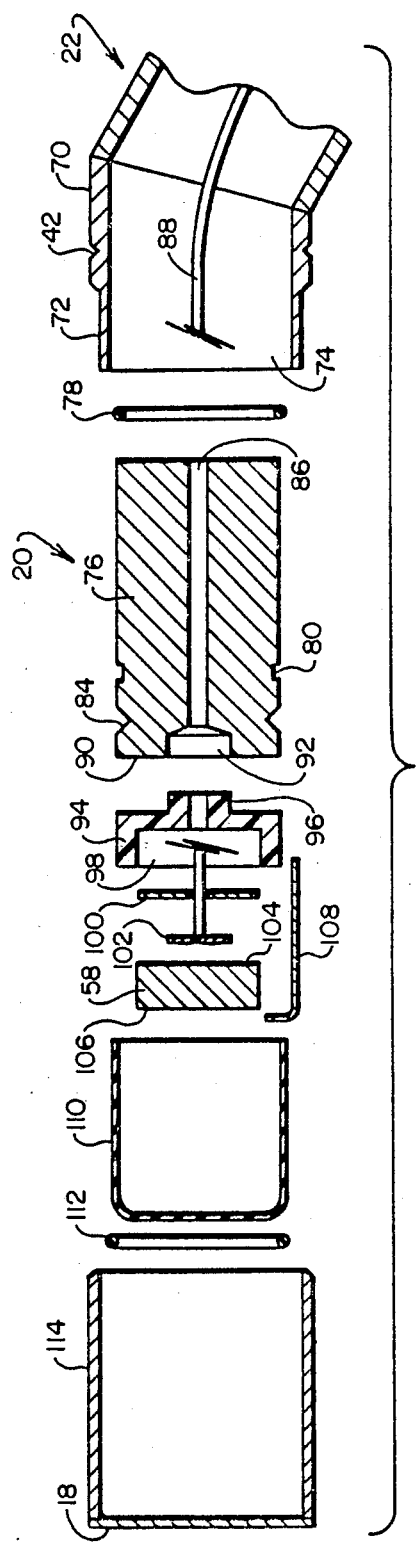

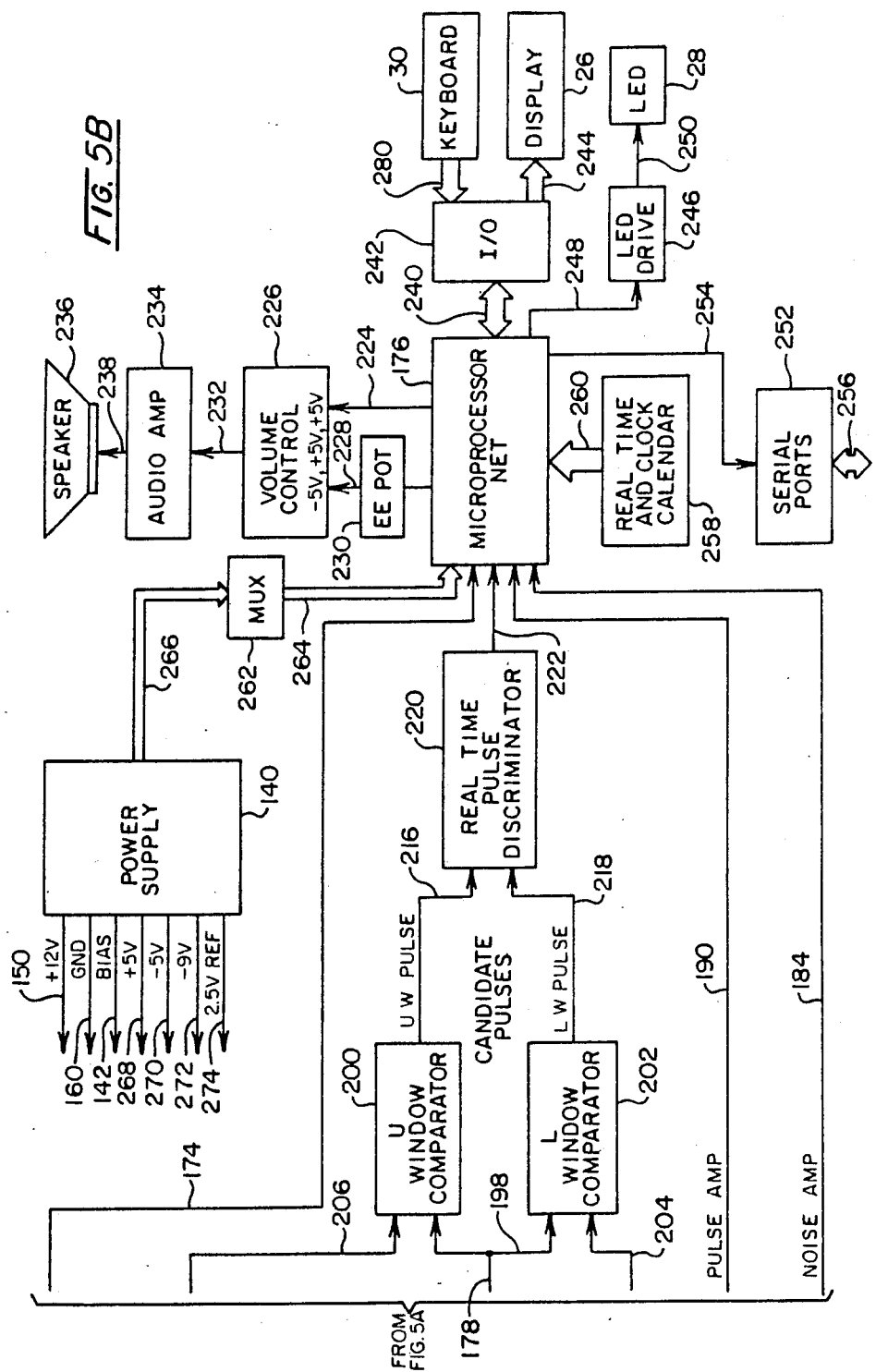

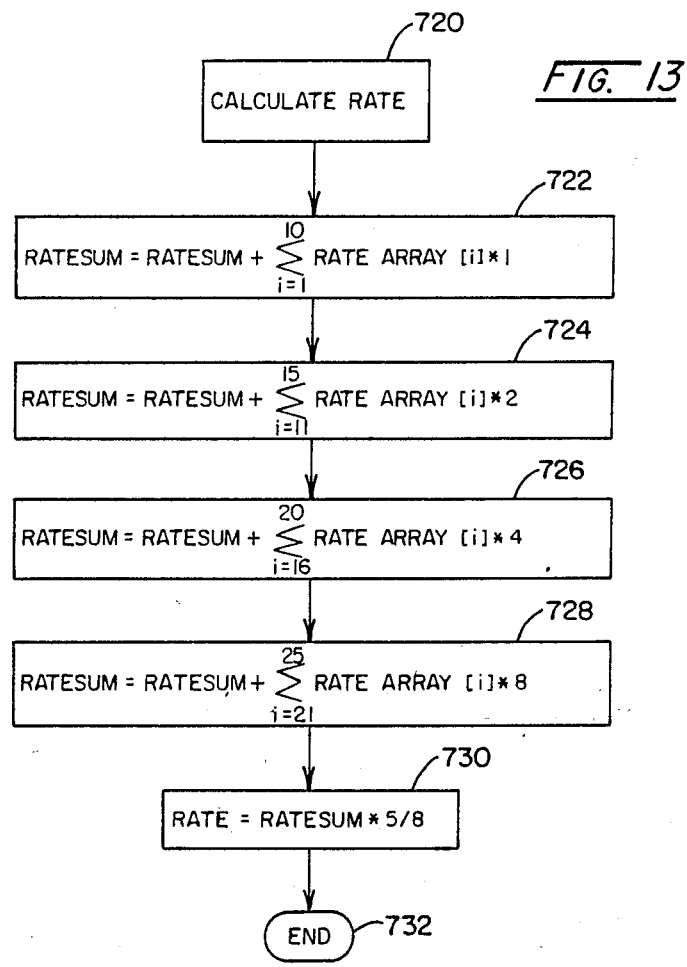

GAMMA RADIATION DETECTOR WITH ENHANCED SIGNAL TREATMENT

BACKGROUND

The detection and treatment of cancerous tissue has been the subject of intense investigation for many years. One among the many approaches to its detection has concerned the identification of tumor specific antigens. Where these antigens can be identified, radionucleid labeled antibodies have been employed which tend to collect at tumor sites. When so concentrated, somewhat elaborate radiation detection equipment then is employed to record, for example, by imaging the concentrations of the emissive substances and thus to locate neoplastic tissue. Important advances in this procedure have been evidenced through the use of monoclonal antibodies or fragments thereof with a variety of radionucleides. Typical techniques for carrying out imaging of these antibodies have involved, for example, tomographic scanning, immunoscintigraphy and the like. The particular choice of radionucleid for labeling antibodies is dependent upon its nuclear properties, the physical half life, the detection instrument capabilities, the pharmacokinetics of the radiolabeled antibody, and the degree of difficulty of the labeling procedure. The most widely used of these radionucleides in nuclear medicine imaging include technetium, $^{99m}Tc$, iodine $^{125}I$, $^{131}I$, and indium, $^{111}In$. Of the above, for localizing tumors of the gastro-intestinal tract, the radionucleid $^{131}I$ is used as the marker of label in conjunction with imaging gamma cameras and the like which are relatively large and elaborate devices positioned above the patient during the imaging process.

In spite of its somewhat extensive utilization, $^{131}I$ is not an ideal radionucleid for use in diagnostic medicine. The high energy gamma-photon emitted from $^{131}I$ is poorly detected by the classic gamma camera and the like instrumentation. In addition, the administered marker emissions deliver a high radiation dose to the patient. Further, the imaging definition of these external imaging devices have not been satisfactory for many reasons. As tumor sites become smaller, the radionucleid concentrations thereat will tend to be lost, from an imaging standpoint, in the background or blood pool radiation necessarily present in the patient.

Over the recent past, a surgical procedure has been developed concerning the differentiation and removal of such neoplastic tissue through the use of much lower energy gamma emission levels for example, $^{125}I$ (27-35 kev). While such a radiolabel cannot be employed with conventional external imaging or scanning devices, because the radiation is strongly absorbed by the tissue intermediate between the tumor and the surface of the patient's body, it has been found that when employed with a probe type detection structure, a highly effective differentiation technique can be evolved. More particularly, the longer half life of this type of radiolabel coupled with a surgical methodology involving the weighting of appropriate intervals from the time of introduction of the radiolabeled antibody to the patient to the time of surgery, can evolve a highly accurate differentiation of cancerous tumor. This improved method of localization, differentiation and removal of cancerous tumor involves a surgical procedure wherein the patient suspected of containing neoplastic tissue is administered an effective amount of a labeled antibody specific for neoplastic tissue and labeled with a radioactive isotope as above-noted exhibiting photon emissions of specific energy levels. Next, the surgical procedure is delayed for a time interval following such administration for permitting the labeled antibody to preferentially concentrate in any neoplastic tissue present in the patient and to be cleared from normal tissue so as to increase the ratio of photon emissions from the neoplastic tissue to the background photon emissions. Thereafter, an operative field of the patient is surgically accessed and tissue within the operative field to be examined for neoplastic tissue has the background photon emission count determined. Once the background photon emission count for the tissue within the operative field has been determined, a hand-held probe is manually positioned within the operative field adjacent tissue suspected of being neoplastic. This technique has been described as "radioimmuno guided surgery" (RIGS), a surgical approach developed by E. W. Martin, Jr., M.D., and M. O. Thurston, Ph.D. For additional information, achieved from probe counting for differentiation. Reference is made to the following technical publications:

| | |
|---|---|
| I. | "CEA-Directed Second-Look Surgery in the Asymptomatic Patient after Primary Resection of Colorectal Carcinoma", E. W. Martin, Jr., MD, J. P. Minton, MD, PhD, Larry C. Carey, MD. Annals of Surgery 202:1 (Sept. 1985 301-12. |
| II. | "Intraoperative Probe-Directed Immunodetection Using a Monoclonal Antibody", P. J. O'Dwyer, MD, C. M. Mojzsik, RN MS, G. H. Hinkle, RPh, MS, M. Rousseau, J. Olsen, MD, S. E. Tuttle, MD, R. F. Barth, PhD, M. O. Thurston, PhD, D. P. McCabe, MD, W. B. Farrar, MD, E. W. Martin, Jr., MD. Archives of Surgery, 121 (Dec., 1986) 1321-1394. |
| III. | "Intraoperative Radioimmunodetection of Colorectal Tumors with a Hand-Held Radiation Detector", D. T. Martin, MD, G. H. Hinkle, MS RPh, S. Tuttle, MD, J. Olsen, MD, H. Abdel-Nabi, MD, D. Houchens, PhD, M. O. Thurston, PhD, E. W. Martin, Jr., MD. American Journal of Surgery, 150:6 (Dec., 1985) 672-75. |
| IV. | "Portable Gamma Probe for Radioimmune Localization of Experimental Colon Tumor Xenografts", D. R. Aitken, MD, M. O. Thurston, PhD, G. H. Hinkle, MS RPh, D. T. Martin, MD, D. E. Haagensen, Jr., MD, PhD, D. Houchens, PhD, S. E. Tuttle, MD, E. W. Martin, Jr., MD. Journal of Surgical Research, 36:5 (1984) 480-489. |
| V. | "Radioimmunoguided Surgery: Intraoperative Use of Monoclonal Antibody 17-1A in Colorectal Cancer". E. W. Martin, Jr., MD, S. E. Tuttle, MD, M. Rousseau, C. M. Mojzisik, RN MS, P. J. O'Dwyer, MD, G. H. Hinkle, MS RPh, E. A. Miller, R. A. Goodwin, O. A. Oredipe, MA, R. F. Barth, MD, J. O. Olsen, MD, D. Houchens, PhD, S. D. Jewell, MS, D. M. Bucci, BS, D. Adams, Z. Steplewski, M. O. Thurston, PhD, Hybridoma, 5 Suppl 1 (1986) S97-108. |

Reference further is made to commonly assigned application for U.S. Pat. Ser. No. 06/905,880 entitled "Method for Locating, Differentiating, and Removing Neoplasms" by Edward W. Martin, Jr., and Marlin O. Thurston, filed September 10, 1986, now U.S. Pat. No. 4,782,640, issued November 8, 1988.

The success of this highly effective differentiation and localization technique is predicted upon the availability of a probe-type detecting device capable of detecting extremely low amounts of radiation necessarily developed with the procedure. In this regard, low energy radionucleides are used such as $^{125}$I and the distribution of radiolabeled antibody with the nucleid is quite sparse so that background emissions can be minimized and the ratio of tumor-specific counts received to background counts can be maximized. Denen, et al., in application for U.S. Pat. Ser. No. 07/027,197, filed March 17, 1987, now U.S. Pat. No. 4,801,803, issued January 31, 1989, and assigned in common herewith describes a probe instrument and related control circuitry having the requisite sensitivity for use with such low energy radionucleides while retaining a robust structuring within a diminutive size suited for the rigorous surgical environment. This probe device is utilized currently under the trade designation "NEOPROBE" instrument.

Typically, the control consoles of radiation detectors such as Geiger counters and the like have functioned to carry out upper and lower energy threshold evaluations of detected impingement of radiation. In practice, each detected impingement is counted and is audibly manifested as a "click" sound. Some detector response circuitry stretches the duration of such abrupt output sounds to develop what may be referred to as a "beep". Similarly, solid-state counter components have been suggested in which, for example, a divide-by-ten function is carried out to adjust the frequency of an audible output from a radiation detector.

Experience in the surgical theater with the Neoprobe detection instrument has shown that the radiation encountered in the course of RIGS procedures is quite random. Where $^{125}$I is employed as a radiolabel or marker and variable intervals of time from marker injection into a patient to the time of surgery are encountered, background-to-tumor ratios may vary widely. These variances also are observed as the probe instrument is maneuvered from tissue region to tissue region in the course of a given surgery. As a consequence, where simple averaging of radiation impingements or "counts" over specified time intervals to derive count rates is employed, an unsatisfactory and somewhat distracting result obtains from an audible readout standpoint. Thus, a development of a relatively consistent system of audible cuing for the surgeon utilizing these probe instruments has been determined to be required. Such a system should avoid development of spurious audible outputs and provide outputs representing a signal treatment exhibiting consistency and reliability such that the surgeon is facilely guided to the situs of tumor.

SUMMARY

The present invention is addressed to apparatus, system, and method for improving detection and location of gamma radiation source concentrations in animal tissue utilizing a hand-held probe. When employed within a surgical theater, audible cuing as to the location of such source concentrations is substantially improved through a generation of audio frequency output as well as the development of count rates of a selectively weighted basis.

With the system, the hand-held probe initially is positioned at a predetermined body region, for example adjacent the heart or aorta, for the purpose of determining a background count rate. The control system associated with the probe develops a background count rate while the probe is so positioned to derive a squelch low count rate. The latter value then is multiplied by a selected range factor to derive a squelch high count rate. These count rates represent the respective lowest and highest frequency selection from a predetermined sequence of frequencies developed from a memory retained frequency table having about 500 frequency entries.

The rate of change of frequency rates is controlled by a slew limiting approach wherein the difference between high and low squelch rate values is divided by a time factor representing, for example, one-half second of time. The resultant squelch delta value then is employed as the limiting rate for frequency changes, an approach substantially improving the audible cuing capability of the system. High and low squelch limits also are developed to improve the response time of the software of the control system.

Another feature of the invention is the provision of a system for detecting and locating gamma radiation source concentrations at specific tissue regions of an animal body further having a predetermined body region selected as emanating gamma radiation at background levels. The system includes a probe which is movable from position to position along the tissue regions and to the predetermined body region which includes a housing having a forward portion extending to a radiation window positionable in the vicinity of the tissue regions and at the predetermined body region. A detector is positioned within the housing for deriving induced charges in response to gamma ray interaction therewith and providing corresponding output signals and a transmission arrangement is included for transmitting the output signals and a transmission arrangement is included for transmitting the output signals. A signal treatment arrangement further is provided in the system which includes an energy level network for validating the output signals and deriving count signals in response thereto. A squelch mode activation arrangement is actuable for deriving a squelch range calibration sequence. Additionally, an audible indicator provides an audible output in response to input signals and a memory is included for retaining count rate data. A control function is responsive to the squelch mode activation actuation and to the count signals derived when the probe is located at the predetermined body region for deriving a basic background count rate. The control further responds to the basic background count rate to derive a squelch count rate value and is responsive to derive the product of the squelch low count rate value and a predetermined range value for deriving a squelch high count rate. The control further responds to retain the squelch low count rate and the squelch high count rate in memory and is responsive subsequently to count signals for deriving count rate signals and for deriving the audible indicator input signals at predetermined frequencies corresponding therewith when the count rate signals exhibit a value intermediate the memory retained squelch low count rate and the squelch high count rate.

Another feature of the invention provides a system for detecting and locating sources of gamma radiation within a region of interest which includes a probe movable from position to position within the region of interest which includes a housing having a forward portion extending from a radiation window positionable in the vicinity of the source, a detector within the housing for deriving induced charges in response to gamma ray interaction therewith and providing corresponding output signals and a transmission arrangement for transmitting the output signals. The system further includes a signal treatment function which includes an energy level network for validating the output signals an deriving count signals in response thereto. A control function responds to the count signals for entering them into a continuously fed queue from earliest to latest received representing a given increment of continuous sampling time, the control effecting a select weight of predetermined time defined increments of count signals within the queue and generating from the weighted count signals a stabilized count rate value. A perceptible indicator provides a perceptible output corresponding with the stabilized count rate value.

Another feature of the invention provides a method for generating audible cuing signals locating gamma radiation concentrations within tissue of an animal body, the body having a region selectable as emanating gamma radiation at background levels. The method includes the steps of:

providing a hand manipular probe movable about the tissue and generating output signals in response to gamma radiation impinging thereon;

positioning the probe at the body region and evaluating the output signals for a predetermined interval to derive a squelch low background count rate;

deriving a squelch high count rate by multiplying the squelch low background count rate by a select range factor;

deriving a squelch difference value as the difference between the squelch low background count rate and the squelch high count rate;

deriving a squelch delta value by dividing the squelch difference value by a predetermined time value;

providing a memory retained table of frequency deriving values from lowest to highest;

providing an audible sound generator actuable to produce a cuing sound output at frequencies of value selected from the table of frequency values;

positioning the probe at select locations of the tissue of the animal body and determining previous and next count rates from resulting output signals;

accessing the table of frequency deriving values in correspondence with the previous count rate as a proportion of the squelch difference to provide a first frequency deriving value;

actuating the sound generator in correspondence with the first frequency deriving value;

determining a rate delta value as the difference between the previous and next count rates;

comparing the rate delta value with the squelch delta value and accessing the table of frequency values in correspondence with a frequency value representing the sum of the previous count rate and the squelch delta value as a proportion of the squelch difference when the rate delta value equals or exceeds the squelch delta value to provide a second frequency deriving value; and actuating the sound generator in correspondence with the second frequency deriving value.

For a fuller understanding of the nature and objects of the particular embodiments of the invention, reference should be had to the following detailed description taken in conjunction with the accompanying drawings.

Other objects of the invention will, in part, be obvious and will, in part, appear hereinafter.

The invention, accordingly, comprises the apparatus, method, and system possessing the construction, combination of elements, steps and arrangement of parts which are exemplified in the following detailed disclosure. For a fuller understanding of the nature and objects of the invention, reference should be had to the following detailed description taken in conjunction with the accompanying drawings.

BRIEF DESCRIPTION OF THE DRAWINGS

FIG. 1 is a perspective view of the probe instrument and associated console representing the instrumentation system of the invention;

FIG. 2 is a side elevational view of the probe instrument shown in FIG. 1 with portions broken away to reveal internal structure;

FIG. 3 is an exploded view of the forward assemblage of the instrument of FIG. 2;

FIG. 4 is a sectional view of the forward portion of the instrument embodiment represented in FIG. 3;

FIGS. 5A and 5B combine as labeled to form a block diagram of the functional components of the control system associated with the probe of the invention;

FIG. 13 is a flow chart showing the technique for calculating count rates according to the invention.

DETAILED DESCRIPTION OF THE INVENTION

Figure 5A:
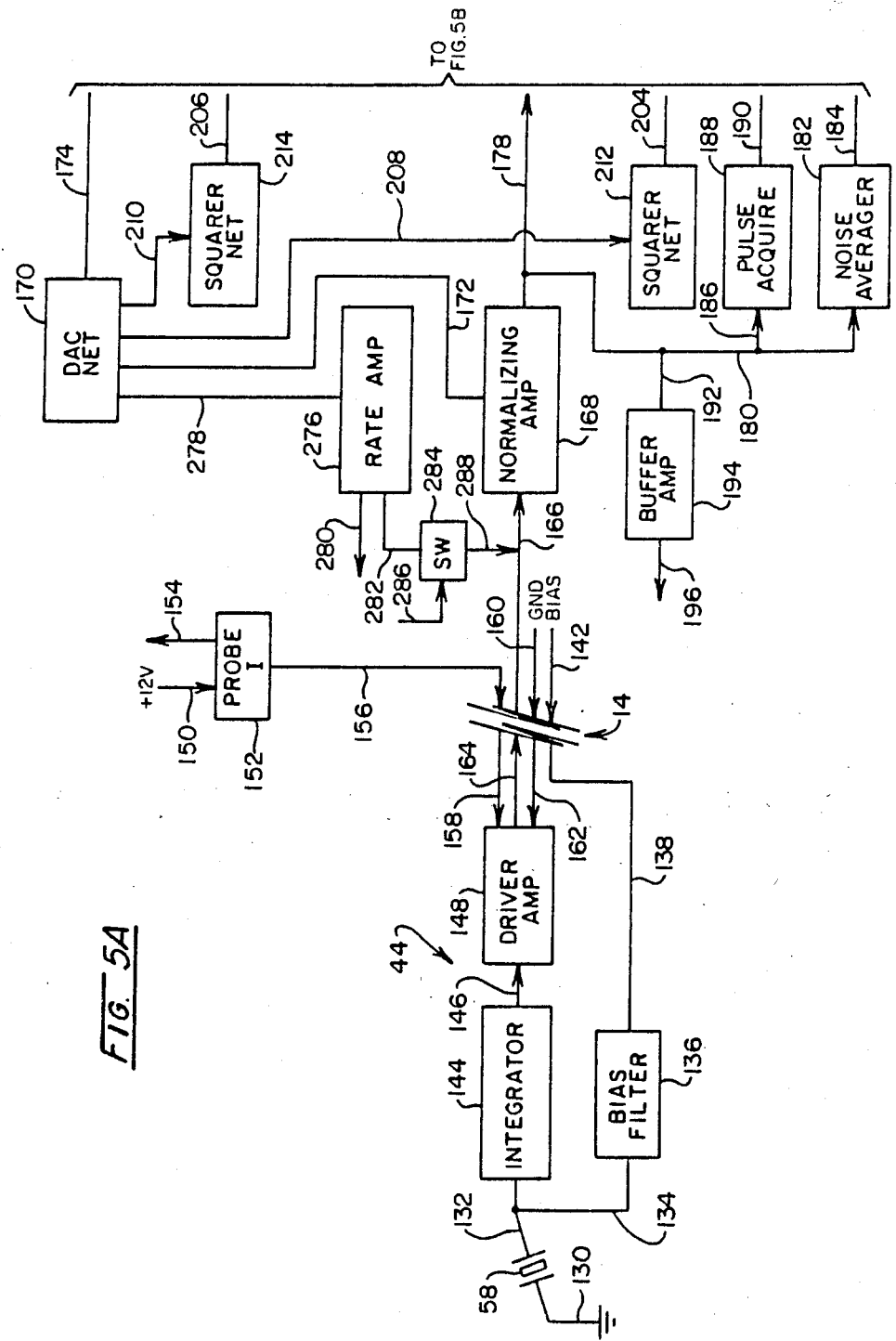

Referring to FIG. 1, an embodiment of the probe and supporting instrumentation of the invention particularly designed for employment in the medical-surgical field is represented generally at 10. This assemblage includes a hand-manipular probe represented generally at 12 which is coupled by a triaxial cable 14 to console 16. The probe 12, which preferably is retained by the surgeon within a disposable polymeric sheath or cover is maneuvered about the region of surgical interest to locate tumorous tissue for resection. When used in conjunction with colonic surgery, for example, the probe 12 is maneuvered through a surgical opening in the body cavity and essentially brought into contact with organs under study by the surgeon. When employed in a radioimmuno-guided mode, a loudspeaker or annunciator within the console 16 provides a "siren" form of output which apprises the surgeon that the probe 12 is at a site of cancer. Thus, it is necessary that the device 12 be of convenient length and comfortable to grasp. The probe 12 is seen to include a window 18 located at the tip of an angularly oriented portion thereof 20. Portion 20 extends from a hand-grippable portion 22 at an angle of about 30° to facilitate its maneuverability about the back or hidden side of organs.

Because the assemblage 10 is used in a surgical theater, the console 16 also is readily cleaned, having a smooth, one-piece touch sensitive polymeric surface 24 surmounting a relatively large LCD readout or display 26, a dual colored LED readout 28 and a sequence of finger-actuated switches each having a tactile feedback. These switches or keyboard as represented generally at 30 as combined with readout 26 permit the microprocessor driven console 16 to carry out an instructive or "user friendly" dialogue with the practitioner. For purposes of safety, the device is powered by a rechargeable battery.

In addition to conventional on and off switches shown, respectively, at 32 and 33, the switches provided on the console 16 include a count mode switch 34, a sound switch 35, a reset count switch 36, a squelch switch 37, a calibration switch 38, and up and down incrementing switches for menu driven user-computer interaction within certain of the switch generated modes as shown, respectively, at 39 and 40.

The probe 12 must be capable of performing essentially at room temperature. Thus, the device employs a cadmium telluride crystal and, because of the preferred low energy levels of radiation which it is called upon to detect, must be capable of operatively reacting to low energy gamma ray interactions. As an incoming gamma ray is absorbed by the crystal, it transfers some or all of its energy to electrons, which as charged particles pass through the semiconductor (crystal) producing electron-hole pairs and, therefore, the capability of charge-transfer within the crystal medium. When a charge particle produces electron-hole pairs in the semiconductor, the electric field causes these charge carriers to move toward and accumulate at the appropriate electrodes. As these charges are collected at the electrodes, they induce a charge or electrical pulse signal in the circuit external to the detector. It is then necessary to pre-amplify these signals and feed them to the electronics of the control unit or console 16.

For effective performances, the probe 12 must be capable of generating and discerning signals representing gamma ray strikes which are of extremely low energy. In this regard, a gamma ray interaction with the cadmium telluride may produce two to four thousand electrons. It being recognized that $6.25 \times 10^{18}$ electrons per second represents one ampere of current, the relative sensitivity of the instant device will become apparent. As a consequence, the mechanical structuring of the mounting arrangement for the crystal within the probe 12 is of importance as is the technique for detecting and treating these significantly small charges representing gamma ray interactions.

Looking to FIG. 2, a more detailed representation of the probe device 12 is revealed. The angular orientation of the front portion 20 is shown having the noted 30° cant with respect to he central axis of the hand gripped portion 22. Device 12 is small having an overall length of about 19 cm and portion 22 having a length of about 12.7 cm. The overall diameter of the cylindrical structure 12 is about 1.9 cm. Front portion 20 is formed having a groove 42 for retaining various "clip-on" devices. Experience to the present, utilizing low energy radiolabeling and achieving very high sensitivity on the part of the probe has removed the need for forward collimation. The hand grip portion 22 carries a preamplifier on an elongate circuit board as represented in general at 44. Depending upon the energies of radiation encountered, the probe 12 structure is formed of an electrically conductive and thus shielding material which functions to attenuate radiation.

Cable 14 supplies power to the preamplifier of the probe, as well as bias to the crystal and functions to transmit the preamplifier treated output signals. The cable includes tin copper cladding components 46 and 48 which are mutually insulated and spaced by a silicon rubber tuber 50 which is somewhat loose to permit flexure. Innermost leads of the arrangement at respective lines 52 and 54 carry the output signals from the preamplifier 44 and a bias signal, for example 30 volts, for application to the rear side of the crystal within the device 12. Clad 46 carries a 12v power supply for the preamplifier circuit, while outer clad 48 carries ground for the system. An outer silicon rubber cover is then provided at 56.

Looking to FIG. 3, an exploded detail of the nose or forward portion 20 of probe 12 is provided. This portion 20 retains a cadmium telluride crystal 58 in a light-tight and mechanically secure orientation while maintaining necessary ground and bias conditions upon it.

FIG. 3 shows the hand-graspable portion as at 22 extending to a supporting tubular portion 70. The forwardly disposed tubular region of portion 70 including cylinder connector surface 72 are configured having an internal diameter defining a cavity or chamber 74. Cavity 74 receives a generally cylindrically shaped slug or clocking arrangement 76 along with an elastomeric retainer layer which retains the slug 76 within the cavity while spacing its outer cylindrical surface from the interior wall of portion 70 an amount sufficient to provide a shock mounting arrangement. This elastomer may be provided, for example, as a rubber epoxy material. To achieve spacing from the noted interior wall and facilitate mounting, an elastomeric ring such as an O-ring is provided as at 78 which serves to hold the slug 76 in an appropriate position while the elastomeric rubber epoxy sets. The O-ring 78 is slid over the copper outer cylindrical surface of slug 78 so as to nest in a rectangular groove 80 formed therein. Looking additionally to FIG. 4, the O-ring 78 is seen in assembled position and the elastomeric retaining layer is shown at 82. Slug 76 is formed of copper or tungsten to attenuate radiation impinging from a rearward direction into the probe instrument 22 and further includes a V-shaped groove 84 extending thereabout. A central bore 86 extends through the slug 76 to carry an insulated lead 88. Lead 88 functions as a bias-signal transmission wire leading to the physically adjacent preamplification stage 44. The forwardmost face of slug 76 provides a base support surface as at 90 which is counterbored at 92 so as to provide an improved connection with a plastic electrically insulative cup or support 94 having a rearwardly disposed cylindrical portion 96 which is nestable within the bore 92. Cups as at 94 may, for example, be formed of a polycarbonate material such as Lexan or the like and, preferably, are adhesively attached to the base support surface 90 and counterbore 92 by a compatible adhesive. Cup 94 includes a central cylindrical cavity 98 which receives and supports an assemblage including a resiliently compressible shock cushion layer 100 as an initial component. Layer 100 may, for example, be formed of a non-woven Teflon (polytetrafluoroethylene) cloth marketed under the trade designation "GORETEX" having a thickness, for example of about 0.020 in. The layer 100 is provided having an opening in the middle thereof for receiving the lead 88. In general, this lead 88 is formed as a multi-strand type and the strands thereof are attached to a small disc 102 of adhesive copper tape. This disk 102 serves to electrically couple lead 88 to and apply a biasing voltage to the rearwardly disposed face 104 of crystal 58. The forward face of crystal 58 as at 106 is electrically grounded by a copper ground strap 108 which extends rearwardly to provide electrical grounding communication with the exterior of copper slug 76. The assemblage of crystal 58, copper adhesive tape or disk 102, shock cushion layer 100, and cup 94 are compressively retained together by an elastomeric retainer 110 which may be provided, for example, as a common finger cot. This sheath of electrically insulative elastomeric material is rolled over the assemblage and retained in position by a resilient band such as a resilient O-ring 112. O-ring 112 nests in the earlier-described V-shaped circumferential groove 84 to retain the sheath 110 in position. The entire assemblage of slug 76 and those parts compressively retained in position by the sheath 110 and O-ring 112 may be maneuvered during the assemblage employing rubber epoxy layer 82 to provide appropriate spacing accommodating for variations in component thickness, for example the thickness variations which may be encountered with crystal 58. The forward assemblage including tube 114 and window 18 then is positioned over surface 72 and cemented in place, for example, with a conductive silver epoxy cement. Note in FIG. 4 that the assemblage is so oriented that a dead space 116 is created between the forwardly disposed surface 106 of crystal 58, as associated with retainer sheath 110, and window 18. This dead air space provides an enhancement of acoustic isolation of the crystal 58.

As represented at circuit 44 in FIG. 2, in order to carry out the treatment of the very faint charges which are evolved due to gamma interaction with crystal 58, it is important that the preamplification function takes place as close as possible to the situs of the interaction. Because of the operational need in surgery for the 30° cant of the central axis of the forward portion 20 with respect to the corresponding axis of the rearward support portion 22 of the probe 12, the small length of transmission wire 88 is required. Because extremely small charges of current are involved in the range of 300–600 attocoulombs, a preamplification stage which performs to achieve a very high gain is called upon but one which performs with low noise generation. In effect, the preamplification stage of the instant apparatus is one achieving a voltage amplification, for example, on the order of about 25,000.

Crystal 58 is maintained in a carefully electrically shielded, acoustically dead and light-tight environment. The outer surface of front portion 20 of the probe instrument 12 is an electrically conductive tube or collar 114 formed, for example, of copper so as to provide a laterally disposed electrical shield, as well as an attenuator for radiation of the energy range contemplated. The forward edge of the tube 114 is closed by the window 18 which is formed, for example, of a silicon-aluminum alloy about 0.015 in. thick soldered thereto. As noted above, the window 18 is selected to permit entry of very low level emissions of gamma radiation. Thus, it is structured to permit the full forward face of crystal 106 to be exposed to such radiation. Even though the window 18 is relatively broad in extent, the capability of the instrument 12 to differentiate the interface between tissue carrying radiolabeled antibodies and the like and those not carrying these labels is quite accurate, when used with low energy marker, i.e. $^{125}I$ is contemplated to the extent that collimation to achieve close differentiation typically is not required.

Referring to FIGS. 5A and 5B, a block diagrammatic representation of the instrumentation circuitry is revealed. In FIG. 5A, the cadmium telluride crystal 58 is shown having one face coupled to ground through line 130, while the opposite, biased face thereof is coupled via lines 132 and 134 to a bias filter represented at block 136. The input to the filter 136 is represented at line 138 as being applied through the triaxial cable as described earlier at 14 and represented by that numeral herein. Line 138 corresponds with the earlier-described line 52 in FIG. 2. This bias emanates from a power supply shown at block 140 in FIG. 5B and represented at line 142.

Line 132 from the crystal 58 is shown extending to an integrator stage 144 of the preamplifier 44. The integrated valuation of detected radiation disturbance then is shown directed as represented by line 146 to a driver-amplification network shown at block 148. A 12v power supply is provided from the power supply 140 (FIG. 5B) as represented at line 150 which, as shown in FIG. 6A, is directed to a probed current network represented by block 152. Under microcomputer control as represented by line 154, the network 152 develops signals, for example, determining whether the probe instrument 12 has been properly connected to the console 16. Delivery of the 12v power supply for the preamplifier stage 44 is represented at line 156 as extending to the driver amplifier from cable 14 via line 158. Line 158 corresponds with the clad 46 described in conjunction with cable 14 in FIG. 2.

Ground to the instrument 12 also is developed from the power supply block 140 as represented at line 160 shown in FIG. 5A as extending to cable 14 and via line 162 to the instrument preamplification components 44. Line 162 corresponds with the earlier-described clad at 48 in FIG. 2.

The output of the preamplification circuit 44 is represented at line 164 extending through the cable representation 14 corresponding with the earlier-described line 54 in FIG. 2. Line 164 extends from the cable 14 as line 166 to the input of a normalizing amplifier represented at block 168. The network represented by block 168 functions to amplify or attenuate, i.e. scale the noise characteristic of any given instrument 12 and normalize the value thereof or render it consistent for later comparison stages. Generally, for example, the 27 kev energy level gamma ray generated pulses in the system will be about five times higher than noise levels. Normalizing amplifier network 168 will establish those noise levels at some predetermined level, for example, 200 millivolts and the resultant proportional valid gamma related pulses will become about one volt high for purposes of ensuing comparison functions. It may be observed that the amplifier network at block 168 is shown controlled from a digital-to-analog converter network represented at block 170 via line 172. Network 170, in turn, is controlled from line 174 extending, as shown in FIG. 5B, to block 176 representing a microcomputer network. The normalized output developed from network 168 is presented along the lines 178 and 180 to a noise averager circuit as represented at block 182. This network 182 determines an average amplitude value for the noise of a given system with a given instrument 12 and provides a corresponding signal as represented at line 184 (noise amp) which is employed as above-described as information used by the microcomputer 176. This information, in addition to being employed with the normalizing amplifier network represented at block 168 may be used to develop a low window valuation for the comparison function.

Line 180 also extends via line 186 to a Pulse Acquire network represented at block 188. This network functions, when activated by the microcomputer represented at block 176, to acquire the value of the highest pulse amplitude witnessed at line 186. Periodically, this information then is transmitted to the microcomputer at block 176 as represented by line 190. Representing a form of peak detector, the network is sometimes referred to as a "snapshot circuit". Also produced from line 180, as at line 192 and block 194 is a buffer amplifier which will provide at line 196 an output representing received pulses which may be made available at the rearward portion of console 16 for conventional radiation evaluation purposes.

Line 178 extends, as shown in FIG. 5B at line 198, to one output of an upper window comparator represented at block 200 and a lower window comparator illustrated at block 202. The threshold level for comparative purposes employed by the network at block 202 is shown asserted from line 204 and, preferably, is developed by the logic of microcomputer network 176 at a level just above the noise amplitude signals generated from line 184. Manual setting of such windows can be carried out. In similar fashion, the upper window of acceptance for valid gamma ray interaction is established from a corresponding line 206. This threshold setting may be made from the information taken from pulse acquire network 188.

Returning to FIG. 5A, the upper window and lower window threshold selections are made under the control of the microcomputer network at block 176 as controlled from the digital-to-analog network shown at block 170. It is the characteristic of such networks as at block 170 to provide an output which is comprised, for example, of 256 steps of varying amplitude. The percentage of incrementation from step-to-step will vary somewhat over the range of voltage values provided. Accordingly, the outputs from this conversion network at block 170, as at lines 208 and 210 are directed to squarer networks shown, respectively, at blocks 212 and 214. These networks function to convert the outputs at lines 208 and 210 utilizing a squaring procedure, providing a voltage squared signal at lines 204 and 206.

Returning to FIG. 5B, the outputs of the comparator networks shown at blocks 200 and 202 represent candidate pulses which may be above or below the given thresholds and are identified as being presented as a "UW pulse" and an "LW pulse" along respective lines 216 and 218. These lines are shown directed to a real time pulse discriminator network represented at block 220 which carries out Boolean logic to determine the presence or absence of valid pulses. Validated pulses are introduced to the microcomputer network 176 as represented by line 222.

The microcomputer represented at block 176 performs under a number of operational modes to provide both audio and visual outputs to aid the surgeon in locating and differentiating tumorous tissue. In the former regard, as represented at line 224 and block 226, a volume control function may be asserted with amplitude variations controlled from a solid-state form of potentiometer as represented at line 228 and block 230. Further, a "siren" type of frequency input signal may be asserted as represented at line 232 to an audio amplification circuit represented at block 234 for driving a speaker as represented at 236 and line 238. With the noted siren arrangement, the frequency of outputs from speaker 236 will be seen to be controlled under an elaborate program designed to maximize the surgeon's ability to pinpoint cancer sites and other regions of enhanced radiation activity depending upon the subject matter being treated. Of course, conventional clicks and beeps can be provided at the option of the operator. Microprocessor 176 may be provided, for example, as a type MC68HC11A8 marketed by Motorola, Inc. This single chip microcomputer employs CMOS technology and includes on chip memory systems including 8K byte ROM, 512 bytes of electrically erasable programmable ROM (EEPROM) and 256 bytes of static RAM. The device also provides on-chip peripheral functions including an eight channel analog-to-digital (A/D) converter, a serial communications interface (SCI) subsystem and a serial peripheral interface (SPI) subsystem. A pulse accumulator also is provided which can be used to count external events (gamma ray related pulses) in an event counting mode.

Microcomputer network 176, as represented by arrow 240 and block 242 also addresses an input-output network which, as represented at arrow 244, functions to provide a pulse count output of varying types as well as outputs represented volume levels, pulse height, noise levels and battery status. Visual readout is represented in FIG. 5B as a block with the same display 26 numeration as described in conjunction with FIG. 1. Similarly, the input-output function represented at block 242 provides appropriate scanning of the keyboard or switches described in conjunction with FIG. 1 at 30 and represented by the same numeration in FIG. 5B. During the counting operation, the microcomputer network 176 functions to control a light emitting diode drive network represented by block 246 from line 248. The drive network represented at block 246 is shown providing an input, as represented by line 250 to the dual LED display as described at 28 in FIG. 1 and represented in block form with the same numeration. This readout provides a red light when a gamma ray is detected and a green light during the counting procedure in general. A serial output port of conventional variety also is provided on the console 16, such ports being represented at block 252 being addressed from the microcomputer at block 176 from line 254 and having output and input components represented by arrow 256. A real time clock-calendar having a non-volatile memory also may be provided in conjunction with the functions of the microcomputer network 176 as represented by block 258 and arrow 260. This memory includes a battery backed up 8K byte RAM facility as well as 32K byte EPROM which are employed in programming the system. Further, the microcomputer may be employed to monitor the performance of the power supply represented at block 140. This is shown being carried out by the interaction of the microcomputer network with a multiplexer represented at block 262 and having an association represented by arrows 264 and 266. It may be observed that the power supply also provides +5v sources for the logic level components of the circuit as represented by line 268; a −5v source at line 270, as well as a −9v reference at line 272 for display 26 drive and, finally, a 2.5v reference as represented at line 274 to provide reference input to analog circuitry.

Returning to FIG. 5B, the microcomputer network as represented at block 176 also provides an input to the digital-to-analog conversion network represented at block 170 which corresponds with the instantaneous pulse rate and this information is conveyed to a pulse rate amplifier network represented at block 276 via line 278. The resultant output as represented at line 280 may be provided, for example, at the rear of the console 16. This circuit represented at block 276 also may be employed to generate a calibrating pulse for testing the downstream components of the system. Thus, the microcomputer applies a predetermined pulse level through the digital-to-analog conversion network at block 170 for presentation to the amplifier network represented at block 276. The resultant output at line 282 is selectively switched as represented by block 284 to define pulse width from the microcomputer input at line 26 to the calibrating pulse at line 288.

Figure 6:
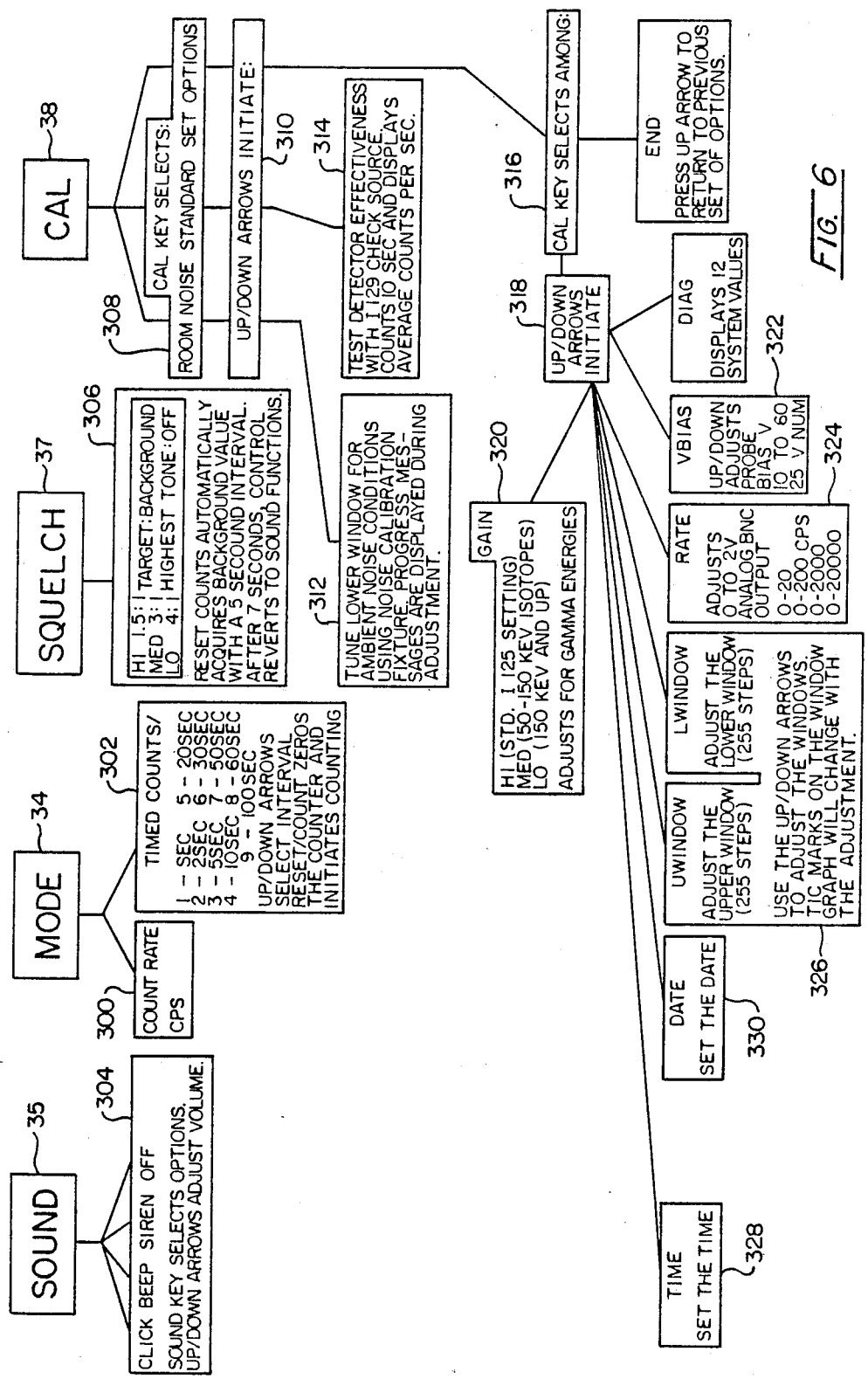
FIG. 6 is a diagrammatic representation of the functions associated with switch actuations carried out for certain switching functions of the control console illustrated in connection with FIG. 1.

Referring to FIG. 6, a diagrammatic representation of the operational functions associated with the principal keys or switches at keyboard 30 as described in conjunction with FIG. 1 are provided. In particular, the functions associated with the principal keys or buttons 34, 35, 37, and 38 are revealed. The count mode key 34 is seen to incorporate two principal forms or modes of counting as represented at blocks 300 and 302. As labeled in block 300, a count rate is available in counts per second. The derivation of this count rate will be seen to be one wherein a selective weighting of count information is carried out. Additionally, as represented in block 302, successive actuation of the up/down arrow key 39 and 40 will permit the operator to select intervals of counting ranging from one second to 100 seconds. Selection of operation as represented in blocks 300 and 302 is by successive actuation of the key 34. The timed counts which are displayed on display output 26 may be reset to initiate counting by depressing the reset count switch 36 as shown in FIG. 1. In general operation, the counting function will default to a count rate arrangement as represented at block 300.

Sound key 35 may be actuated as represented at block 304 to provide a "click" type sound familiar to Geiger counters and the like, a "beep" sound, a tone as represented by the term "siren" or a muting or turning off of the sound. These options are elected by successive actuations of key 35. Additionally, the noted up/down arrows 39 and 40 may be used to adjust volume of the sound output.

The squelch button 37 is employed by the practitioner to automatically adjust the system to the background radiation emanating from a given patient. As noted earlier, this background value will vary from patient to patient and organ to organ. As outlined in block 306, typically, the surgeon positions probe 12 at a predetermined location on the body to carry out a background evaluation. For example, the probe 12 often is positioned in the region of the heart or aorta to obtain a representative background count. Once so positioned, the reset count switch or button 36 is actuated and the control system acquires a background count value with respect to the patient over a five second interval. The information so developed is then used to generate upper and lower squelch threshold values in accordance with a range selection made by actuation of switch or button 37 and selected as high, medium, or low. For a high range selection, the ratio between the squelch high threshold and squelch low thresholds is at 1.5:1. Similarly, a medium range is at 3:1, while a low range is at 4:1. Operation in this manner also automatically elects a siren form of sound which is developed from a tabular organization of frequencies ranging from 60 Hz to 3500 Hz. Thus, for a high range selection, the surgeon essentially is apprised of the presence of cancer or the nonpresence of cancer inasmuch as the entire frequency range is between a very narrowly spaced squelch threshold levels. In the event the reset count switch 36 is not actuated within seven seconds, the system reverts to a normal count mode employing the siren sound effect with a count rate in counts per second associated therewith as represented at block 300.

Because of the intensity of mental concentration of the part of the surgeon during the major forms of surgery with which the instant system is employed, it is necessary that the audible information, i.e. cuing supplied by the system be as reliable and informative as possible. Because of the unusual randomness of the radiation encountered in this form of procedure, the rate of audible reporting of count rates is confined within slew rate limits. Additionally, the system will reject count rates falling momentarily above and below a predetermined level in order to be able to recover quickly from a software standpoint from aberrational count rate excursions. Without such control techniques, the surgeon may otherwise be called upon to wait in the course of a surgical procedure for a period of up to, for example, two seconds for a recovery of the system to occur. Also important is the development of a uniformity of sound output for a given probe scanning situation. By employing a tabular retained sequence of frequencies which operate within the high and low squelch level differential, a highly desirable consistency of performance is achieved. Specifically, when the average count rate is below the lower squelch setting no sound is produced. When the average count rate is between the lower and upper squelch setting the pitch of the sound increases with count rate. Above the upper squelch setting a nearly continuous sound is produced.

The calibration button or switch 38 is seen, as represented at block 308, to provide a menu approach to carrying out a variety of calibration procedures. In this regard, as represented in block 308, room noise may be evaluated where desired, a standard calibration may be carried out, and a grouping of options may be selected. Access into the menu driven calibration procedure is provided by actuation of the up/down arrow keys 39 and 40 as represented at block 310. With respect to room noise, as represented at block 312, a shield of noise calibration fixture may be employed to avoid erroneous calibration that might result from a nearby source of radiation. Prompts are provided at display 26 during the course of this procedure. Block 314 represents a standard calibration arrangement wherein detector effectiveness may be tested with a check source, for example carrying a small amount of the isotope $I^{129}$.

The options available in setting the system up also are available as represented at block 316 by actuation of the calibration key or button 38 and the up/down buttons 39 and 40 as represented at block 318. Thus, the gain of the system may be set as represented at block 320, voltage bias asserted at the crystal 58 may be adjusted as represented at block 322. An analog output provided at the rear of the console or housing 16 may be provided as represented at block 324 and the noted upper and lower window comparator levels as described in conjunction with FIG. 5B at respective blocks 200 and 202 may be adjusted as represented at block 326. Finally, the time of days as well as the calendar date may be adjusted by the operator as represented by respective blocks 328 and 330.

Figure 7:
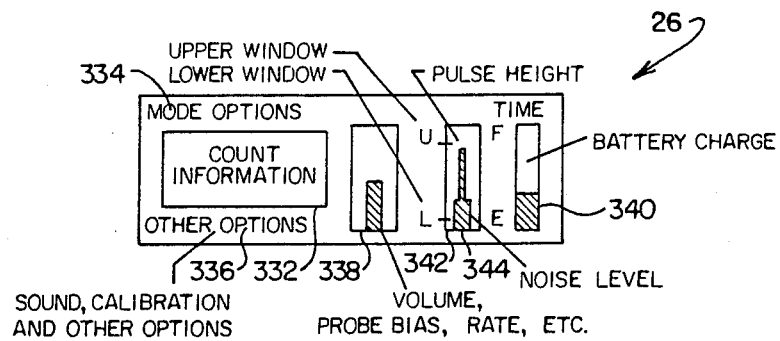
FIG. 7 is a schematic representation of data made available in the display of the control console represented in FIG. 1.

Looking to FIG. 7, the general visual readout provided from display 26 is illustrated in a functional manner. Numeric data such as count information is provided within the boundary represented at 332, while a selected count mode such as rate or time counts is displayed at the region represented at 334. The type sound selected such as siren or the like as described at block 304 is displayed at region 336 along with calibration option information and the like. A general bar graph which provides relative information as to volume, probe bias rates and so forth is developed within the boundary 338, while the extent of battery depletion is represented in bar graph form at boundary 340. A relative representation of upper and lower window levels as described in conjunction with blocks 200 and 202 is provided by tick marks associated with the respective letters U and L as shown generally in conjunction with boundary 342. This same boundary also displays pulse height as a narrow bar while noise level is represented by a wider representation, the combined bar chart being represented at 344.

Figure 8A:
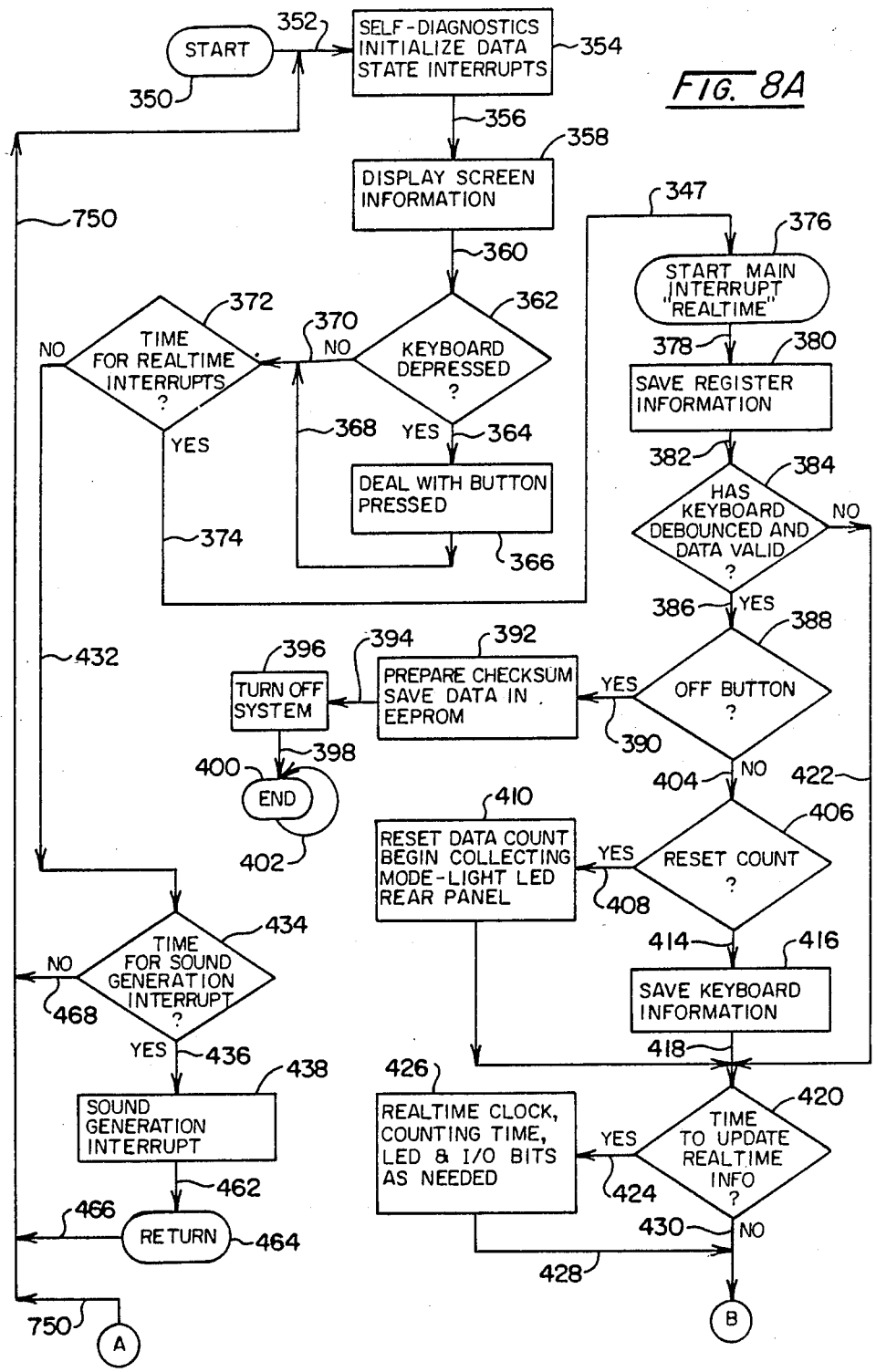
FIGS. 8A and 8B combine to provide a flow chart describing the control program of the system of the invention.
Figure 8B:
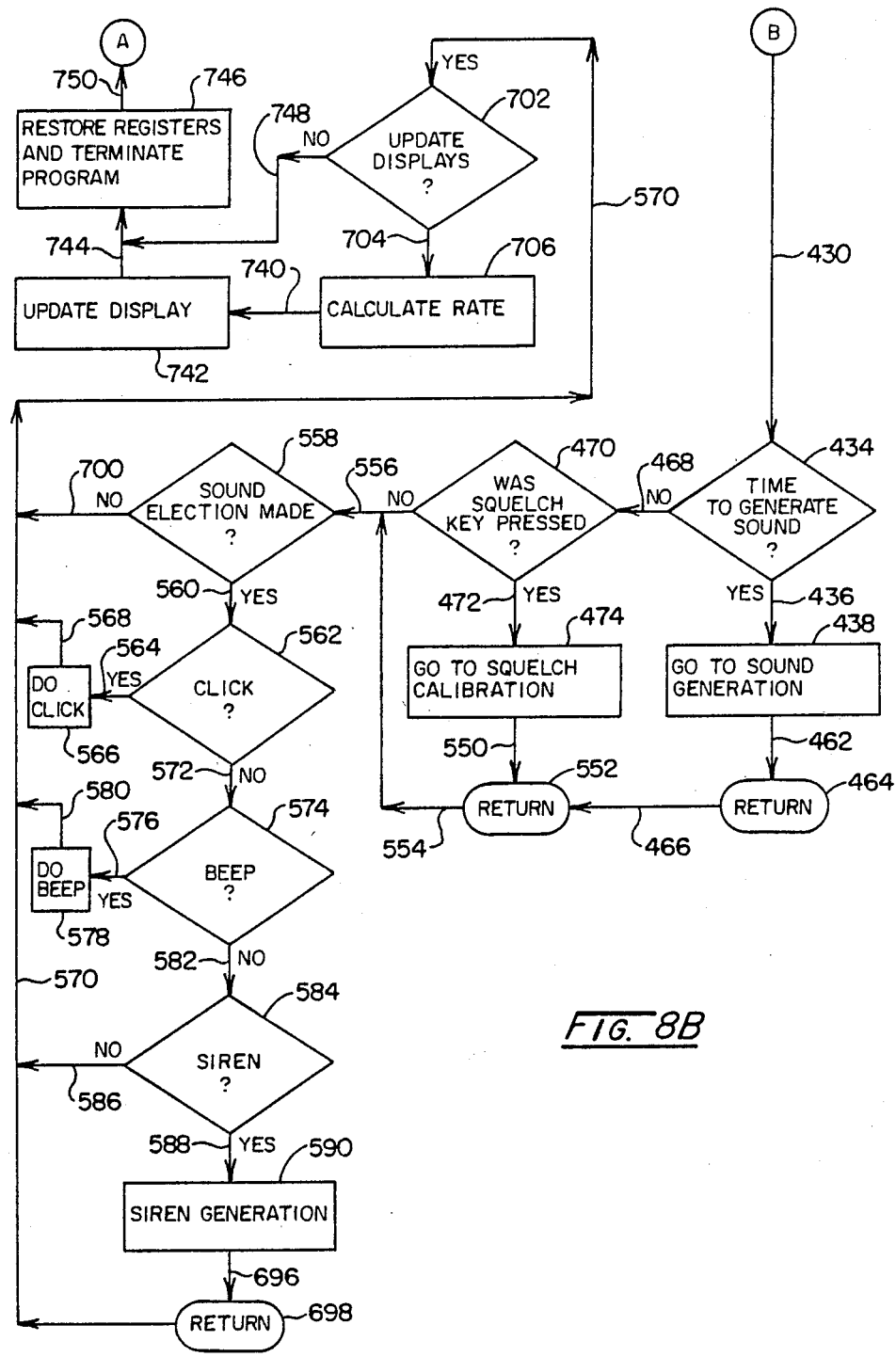

A general program under which the microprocessor network 176 performs is represented in flow chart format in figures 8A and 8B. Referring to the former figure, the start of the main program is represented at node 350 which is shown directed via line 352 to the self-diagnostic and initialization procedures represented at block 354. Following such initialization, as represented at line 356, the program proceeds to display screen information to the operator as represented at block 358. This information is introductory, for example representing a salutation, copyright notice, and the like. As represented at line 360 and block 362, the program then determines whether or not a key or switch button within the keyboard 30 has been depressed. In the event that it has, then as represented at line 364 and block 366, that switching action is dealt with in terms of a user interface activity wherein the screen 26 is updated, proper modes are selected, and the like. As represented at line 368, the program then commences performance in conjunction with a sequence of real time interrupts which occur, for example, at a rate of 50 times per second. Thus, the program continues as represented at line 370 to the inquiry at block 372 wherein a determination is made whether the time has arrived for the occurrence of a real time interrupt. Note, additionally, that with a negative determination at block 362, this same inquiry at block 372 is carried out as represented at line 370. In the event that a real time interrupt is to occur, then as represented at line 374 and node 376, the commencement of the main interrupt, "real time" activities ensues. As represented at line 378 and block 380, the interrupt driven routine of the program initially saves register information and then, as represented at line 382 and block 384, carries out a test as to whether the key information obtained is valid. For example, a key in general is required to be pressed for 20 milliseconds for validity of input. In the event of an affirmative response, as represented at line 386 and block 388, a filtering function is carried out to determine whether or not the off switch 33 has been depressed. In that event, then there is no rationale for continuing with the active program.

Thus, assuming that the off button has been depressed, as represented at line 390 and block 392, a checksum is prepared to assure that the data in memory are valid and the information then is saved in non-volatile memory RAM (Block 258), it being recalled that the microprocessor employed at 176 has 512 bytes of such non-volatile memory. The program then proceeds, as represented at line 394 and block 396 to turn off the system, whereupon as represented at line 398 and node 400, the interrupt routine is ended. Loop 402 is shown extending from node 400 to line 398 to represent an infinite loop form of ending to assure maintenance of routine alignment during shut-down.

Assuming that the off button was not actuated, then as represented at line 404 and block 406, the program determines whether the reset count switch 36 of console 16 has been depressed. This switch is an actuator which commences a given count sequence from an initial or zero level. In the event that the reset count button 36 has been actuated, then as represented at line 408 and block 410, the data count is reset to zero, the LED 28 on console 10 is energized or illuminated to a green color and a collecting mode for data ensues. Additionally, an I/O bit update is provided at a terminal (not shown) at the rear panel of console 10. The program then continues as represented at line 412.

In the event that no reset count button 36 actuation has been observed, then as represented at line 414 and block 416, switch information is saved and the program continues as represented at line 418 to the inquiry at block 420 to determine whether it is appropriate to update the display 26 and real time clock information. Also associated with line 418 is path line 422 from block 384 showing that the program defaults to this position in the event that no valid switch actuation has been detected. Additionally, line 412 from block 410 is shown entering the program at line 418. In the event that the appropriate timing is at hand to update the real time information, then as represented at line 424 and block 426, the real time clock is updated, the lapsed counting time is updated, and the LED 28 and I/O bits are altered as required. Following such update, as represented at line 428, the program returns to line 430 also representing a determination that time for updating has not occurred as developed at the inquiry at block 420.

Returning momentarily to the inquiry at block 372, where the time for a real time interrupt is not at hand, a short subroutine for sound generation may be called. Thus a negative determination at block 372 leads as represented at line 432 to the inquiry at block 434 to determine whether or not a time for generating a sound has occurred. In the event that it has, then as represented at line 436 and block 438, the program enters a "sound generation" subroutine developing a component for the generation of a requisite sound element to activate speaker 236 (FIG. 5B).

Figure 9A:
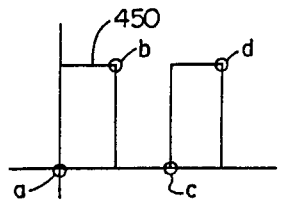
FIG. 9A is a schematic representation of a square-wave generated by interrupts in accordance with the sound generation components of the invention.
Figure 9B:
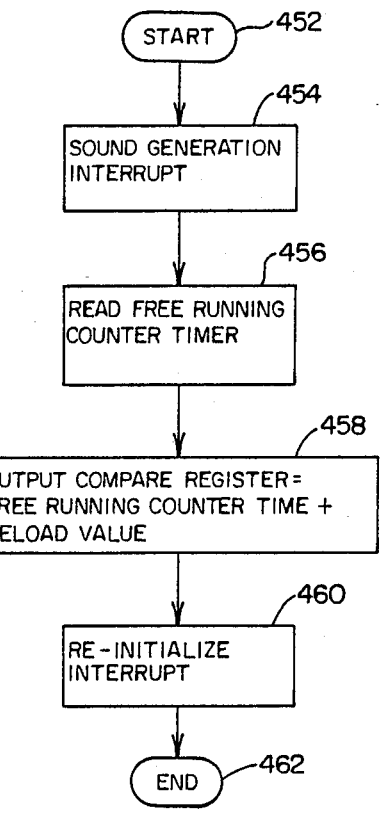
FIG. 9B is a flow chart showing a sound generation interrupt technique according to the invention.

The sound generation technique employed by the program is one wherein a binary signal is generated at a given output port at a rate developing an appropriate squarewave frequency which, in turn, is by the hardware represented at FIG. 5B filtered to remove harshness otherwise occasioned by the harmonics involved prior to the driving of speaker 236. Looking to FIG. 9A, a schematic representation of the occurrence of such interrupts is represented in general at squarewave curve 450, exemplary interrupt transitions for the curve being represented at a–d. Turning to FIG. 9B, the subroutine is portrayed as entering from node 452 as represented at block 454. Curve 450 reveals that the interrupt occurs twice as fast as the frequency output generated. As a first step in this short routine, a free running counter timer of the microprocessor network is read as represented at block 456. To this value extant at the free-running counter timer a reload value is added and, as represented at block 458, an output compare register of the microprocessor network 176 then seeks to compare the value at the free running counter timer with the summed value including the reload value. When equivalency occurs as determined by the output compare register, an interrupt is carried out and, as represented at block 460, the interrupt register is reinitialized. The short subroutine then ends as represented at node 460. As an example of the technique employed, where it is desired to generate sound at a frequency of 1 KHz and the system clock occurs at 1 MHz, the reload value will have been established to generate two interrupts per cycle or 2,000 interrupts for each 1,000 Hz. The reload value to achieve this then is the result of dividing 1 MHz by 2,000 or a value of 500. Thus, each interrupt will occur every 500 clock cycles of the system clock. This short subroutine is employed for all audible outputs of the system, including the noted siren sound, "clicks" as well as "beeps".

As shown in FIG. 8A, following the completion of the sound generation routine, as represented at line 462, return node 464 and line 466, a return condition ensues, the instant subroutine being called upon often in the course of the main program.

Returning to blocks 420 and 426, line 428 is seen extending to the inquiry represented at then as represented at line 468 and block 470 in FIG. 8B where, a determination is made as to whether the squelch key 37 on console 10 had been actuated. This key is employed for the purpose of establishing background levels in a patient by, for example, placing the probe 12 adjacent a predetermined body region, for example the heart or aorta. The form of ranging or calibration carried out is particularly intended for use with the siren form of audible cuing. In the event that the squelch key or button 37 has been actuated, then as represented at line 472 and block 474 a squelch calibration subroutine is entered.

Figure 10:
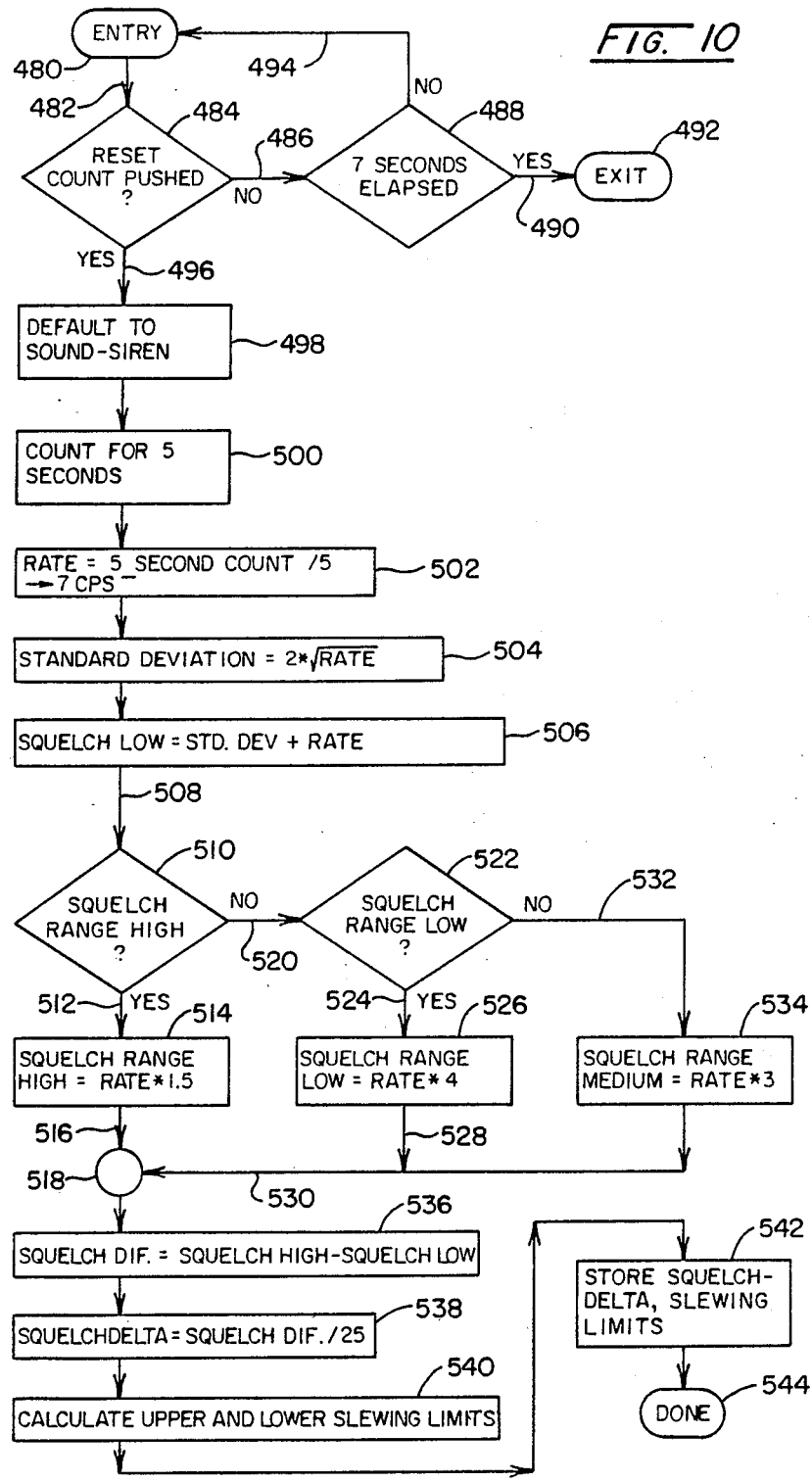
FIG. 10 is a flow chart showing a squelch calibration routine employed with the system of the invention.

Referring to FIG. 10, this subroutine is illustrated as entering at node 480 and, as represented at line 482 and block 484, an inquiry is made as to whether the reset count button 36 has been actuated. In the event that it has not, then as represented at line 486 and block 488, a determination is made as to whether seven seconds has elapsed. In the event that it has, then the exit is made from the subroutine as represented at line 490 and exit node 492. During the seven second time out, as represented at line 494 extending to line 482, a delay loop is executed awaiting the actuation of reset count switch 36. Upon the actuation of reset count button or switch 36, as represented at line 496 and block 498, the subroutine defaults to the siren form of sound output and, as represented at block 500, a count is carried out to determine background rate for a period of five seconds. Following this five second count procedure, as represented at block 502, a basic background count rate is developed from the background count by dividing the total count by five seconds to derive a counts per second valuation. The subroutine then computes a reference deviation of the count rate developed at block 502 as represented at block 504. This reference deviation is computed as twice the square root of the count rate. The reference deviation then is added to the computed count rate as represented at block 506 to develop a basic background count rate identified as "squelch low" which is submitted to memory. As described in conjunction with block 306 in FIG. 6, the surgeon may select a range value for deriving a squelch high count rate based upon the computed squelch low value. In this regard, the subroutine is seen to progress as represented at line 508 to the query posed at block 510 determining whether a high range has been elected. This range provides for a squelch high value which is 1.5 times the squelch low value. When so elected, the siren type sound generation will be selected from a look-up table wherein frequencies will range from a low of about 60 Hz to a high of about 3500 Hz for that range extant between the squelch low value and squelch high value. In practical effect, the higher frequency will be heard by the surgeon at such time as the probe 12 is moved adjacent tissue carrying a marker. This is a form of cancer present versus cancer not present "binary" audio cuing which has been found to be desired by surgical practitioners. Thus, in the event that a squelch high is elected, as represented at line 512 and blocks 514, the squelch high value is developed as the squelch low rate times 1.5. The program then continues as represented at line 516 to the junction represented at node 518.

In the event that the squelch high range is not elected to provide a negative response to the query at block 510, then as represented at line 520 and block 522, an inquiry is made as to whether the squelch low range has been elected by actuation of switch of button 37. In the event that it has, then as represented by line 524 and block 526, the squelch high range is computed as the product of the squelch low rate times 4. The subroutine then continuous as represented by lines 528 and 530 to the junction point node 518. Where the inquiry at block 522 is in the negative, then a medium range has been elected and as represented by a line 532 and block 534 a squelch medium range is computed by multiplying the squelch low rate times a factor of 3. The program then continues to junction node 518 as represented at line 530. From node 518, as represented at block 536, the difference between the squelch high computed value and squelch low computed value is computed and identified as "squelch difference". The routine then computes a value of "squelch delta" as represented at block 538 which is the computed value for squelch difference divided by a predetermined rate limit value, here selected as 25. In this regard, by selecting the latter value for division, and considering an update of rate 50 times per second for the program, a possible range from lowest tabular developed frequency to highest tabular developed frequency becomes about one-half second. In effect, a slew rate limit is computed representing change in rate over change in time or counts per second per second. This slew rate limitation improves the reliability and quality of the audible cuing in siren mode, eliminating frequency excursions and the like which distract as opposed to aid the surgeon during the intense concentration of surgery. Because of the randomness of radiation encountered in the surgical theater, the system also limits the rates which can be computed by supplying a factor to the squelch high and squelch low valuations. As represented at block 540, these upper and lower slewing limits are computed, for example, as being 10% above and below the respective squelch high and squelch low values. The value for squelch delta as well as the noted slewing limits then are stored in memory as represented at block 542 and the subroutine is completed as represented at node 544.

Returning to FIG. 8B, the squelch calibration subroutine is shown to return to the program as represented by line 550, return node 552 and line 554 extending to line 556. In the event that the squelch key or button 37 has not been actuated as represented at block 470 and the latter line 556, the program then inquires as to what form, if any, of sound cuing election has been made by the operator as represented at block 558. If such an election is made, then as represented at line 560 and block 562, a determination as to whether a click type of sound is to be generated. Such a click emulates the sound typically heard in a conventional Geiger counter. In the event that a click type sound is elected, then as represented by line 564, and block 566, a click type sound will be carried out. The click sound is a macro routine which serves to generate, for example, a frequency of 1,000 Hz over an interval of 20 milliseconds employing a predetermined fixed reload value discussed in conjunction with FIG. 9B. The program then continues as represented by lines 568 and 570.

Where a determination that a click type sound output has not been elected, then as represented by line 572 and block 574, a determination is made as to whether a beep form of sound output has been elected. Where that is the case, than as represented by line 576 and block 578, a macro routine is called upon to provide a reload value for sound generation deriving, for example, an output of 1,000 Hz for about 50 milliseconds. The program then continues as represented by lines 580 and 570.

Where the determination at block 564 is in the negative, then as represented by line 582 and block 584, a siren type sound may be elected. In the event that the siren form of sound is not chosen, then as represented by lines 586 and 570 the program continues. However, in the event that the siren form of sound is being utilized, then as represented by line 588 and block 590, a siren generation routine is carried out.

Figure 11:
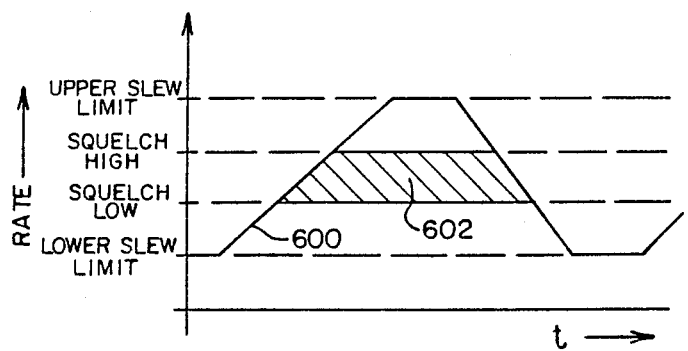
FIG. 11 is a schematic representation of a technique for controlling audible cuing in accordance with the invention.

The siren form of sound generation employs the earlier described squelch delta values as well as the upper and lower slew limits to achieve an effective audible cuing for the surgeon. Looking to FIG. 11, the controls over sound output for the system at hand are revealed in graphic fashion in which count rate is plotted schematically against time. In the figure, the acceptable count rate is shown by curve 600 to commence at a lower slew limit below which the system will not compute count rate. Above that value, as labelled "squelch low", the system will commence to create sound from the earlier-noted table containing range of sounds which are employed from a low entry developing about 60 Hz to a high entry developing about 3500 Hz, about 500 table entries being incorporated between those two limits. The squelch high level also is labeled in the graph as well as the upper slew limit above which count rates are not computed. The slope of curve 600 represents the maximum change of frequency with time and, accordingly, the region represented at 602 is that wherein variable sound can be developed. Above the squelch high level, the sound is continuous.

Figure 12B:
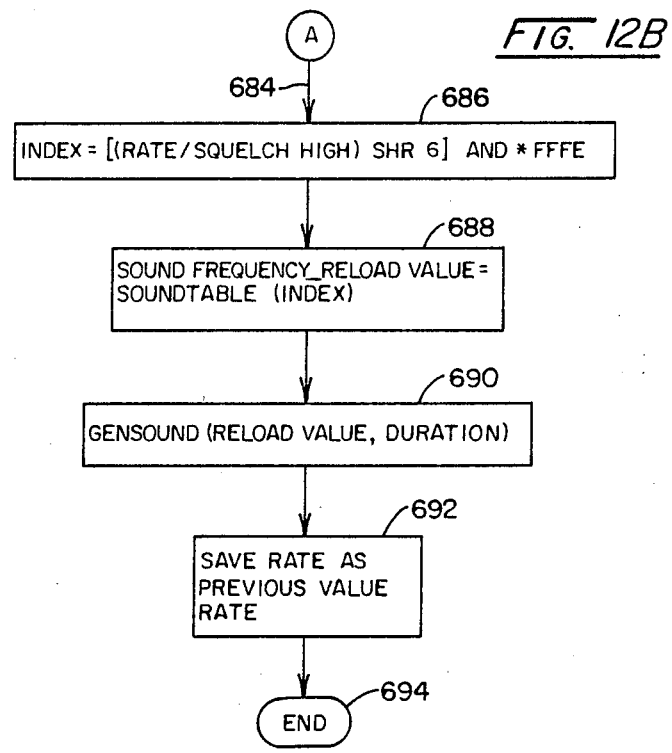
FIG. 12 is a flow chart showing a siren sound generation employed with the system of the invention.
Figure 12A:
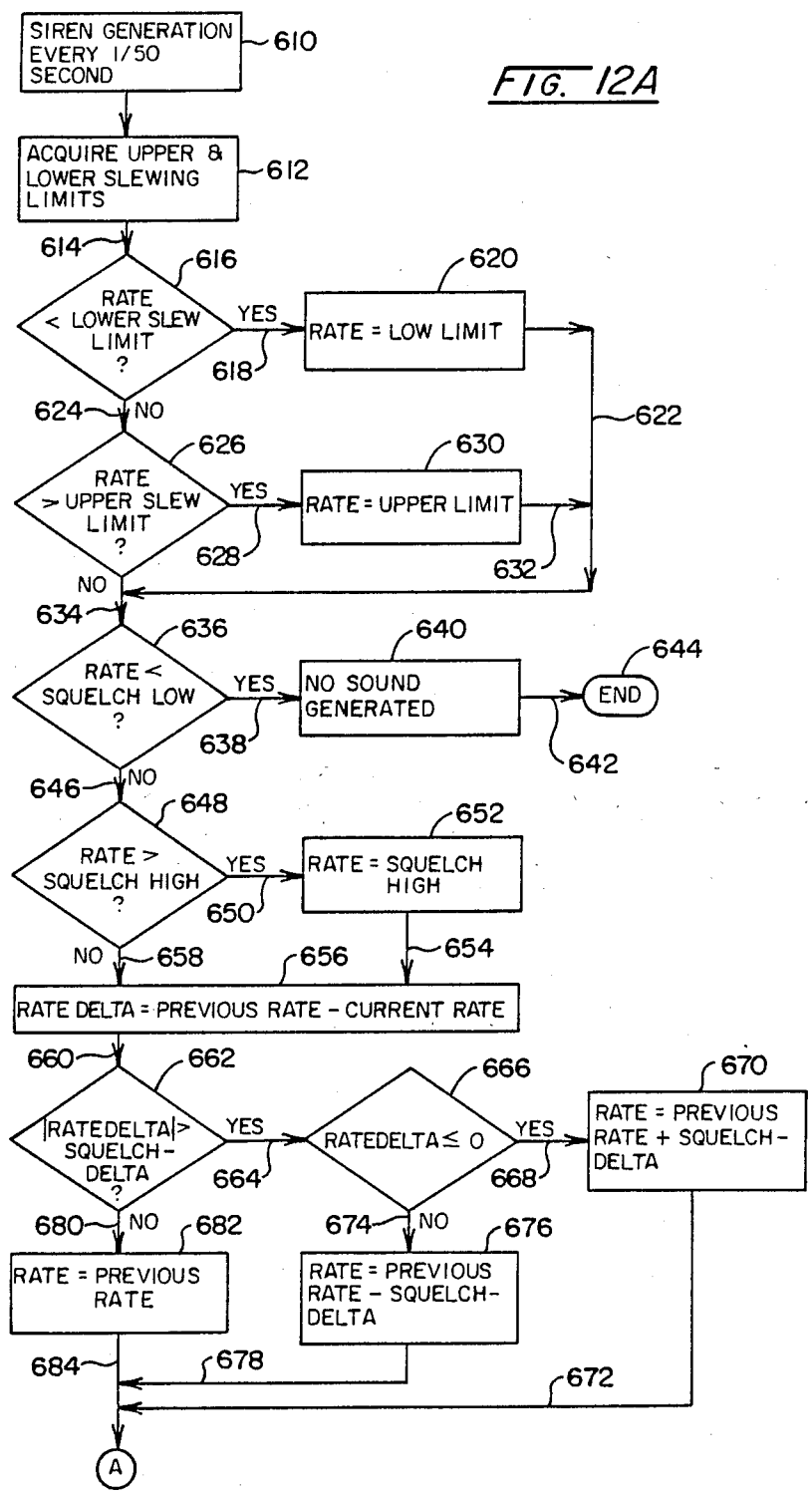

Turning to FIG. 12A, the sound generation routine is shown commencing in conjunction with block 610 which identifies the siren generation as occurring at an update rate of 50 times per second. The program commences with an acquisition of the noted upper and lower slewing limits as represented at block 612 and as were computed as described in conjunction with block 540 of FIG. 10. Upon acquiring these limits, as represented by line 614 and block 616, a determination is made as to whether the computed count rate is lower than the lower slew limit. In the event that it is, then as represented by line 618 and block 620, the rate selected by the system is that of the lower limit as earlier computed and acquired. The program then continues as represented by line 622. Where the computed rate is not lower than the lower slew limit, then as represented by line 624 and block 626, a determination is made as to whether the computed count rate is greater than the upper slew limit. In the event that it is, then as represented at line 628 and block 630, the count rate selected is that representing the upper limit as discussed at block 540 in conjunction with FIG. 10. The program then continues as represented by lines 632 and 622. Where the inquiry at block 626 is in the negative, then as represented by line 634 and block 636, a determination is made as to whether the computed rate is less than the squelch low value. Where that is the case, then as represented by line 638 and block 640, no sound is generated and as represented by line 642 and node 644, the routine ends. Where the determination at block 636 is that the rate is not at a level below the squelch low value, then as represented by line 646 and block 648, a determination is made as to whether the computed count rate is greater than the squelch high value. In the event that it is, then as represented by line 650 and block 652, the count rate is made equal to the earlier-developed squelch high value. The program then continues as represented at line 654 to carry out the instructions represented at block 656. Similarly, in the event of a negative determinations with respect to the computed rate being greater than the squelch high value, as represented at line 658, the program also continues to the instructions represented at block 656 wherein a rate delta is computed as the value of the next previous rate selected less the current rate. This is a commencement of the slew rate limitation as represented by curve 600. Following a computation of rate delta, as represented at line 660 and block 662, a determination is made as to whether the absolute value of the earlier computed rate delta is greater than the compound squelch delta value. If that is the case, then a change in frequency would be called for depending upon the presence of an increasing or decreasing count rate. Accordingly, in the event of an affirmative determination, as represented by line 664 and block 666, a determination as to whether the rate delta is less than or equal to zero is made. In the event that it is, then as represented by line 668 and block 670 the rate selected is made equal to the previous rate plus the squelch delta value which will permit a selection of a larger value frequency, it being recalled that a negative rate delta corresponds with such a condition, inasmuch as the current rate is subtracted under the instructions of above-discussed block 656. The program then continues as represented at line 672. Where the determination at block 666 is that the rate delta is greater than zero, then as represented by line 674 and block 676, the selected count rate is made equal to the previous rate less the squelch delta valuation corresponding with a decreasing frequency output. The program then continues as represented by line 678.

Returning to block 662, where the absolute value of rate delta is not greater than the value of squelch delta, then as represented by line 680 and block 682, the selected rate is made equal to the previous rate and the program continues as represented by line 684 and node A to carry out an index determination as represented at block 686 (FIG. 12B). The index provides for access to the noted frequency table and is computed as the rate selected divided by the squelch high value which will represent a number between 0 and 0.999 which is submitted to a shift register and is then masked with respect to the lower bits by the hex value FFFE. The program then continues to access the reload value for sound generation as represented at block 688 and, following accessing the reload value, represented at block 690, the sound generation routine as described in conjunction with FIG. 9B is called. The routine then continues as represented at block 692 to save the currently computed rate as the previous rate valuation, whereupon, as represented at node 694, the routine ends.

Returning to FIG. 8B, the return from the siren generation routine as represented at block 590 is, in turn, depicted by line 696, node 698, and line 570. Where no sound election is at hand as determined in conjunction with block 558, then as represented at line 700, the program considers the inquiry represented at block 702 wherein a determination is made as to whether the display is to be updated. Where that is the case, then as represented by line 704 and blocked 706, the count rate is calculated. Because of the random nature of the counts received, the select weighting of predetermined increments of counts received is made as part of the rate calculation used in conjunction with sound generation and the like. In effect, simple averaging of counts over an interval of time, for example one-half second or the like has been found to require excessive time in order to acquire a proper count rate average. Thus, the weighting approach representing in the flow chart of FIG. 13 was developed. In effect, the count rate is calculated for each 100 milliseconds and that rate then is stored in a rate queue which is constantly being updated. The rate queue carries about one-half second's worth of data or counts and these counts are weighted from oldest to newest and the sum of the weighted counts then is multiplied by a scaling factor. FIG. 13 shows the rate calculation subroutine as entering at block 720 and commencing with the instructions at block 722 wherein the ten oldest count entries are summed and given a weight of unity. The next rate summation is represented at block 724 wherein a next following five entries from 11 through 15 are summed and weighted by a factor of 2. The subroutine then proceeds to the weighting approach shown in block 726 wherein the next five entries representing counts are summed and weighted by a factor of four and finally, as represented in block 728 entries 21 through 25 representing the newest count valuations are summed and weighted by a factor of eight. The resultant total weighting then amounts to 80 for 25 counts. As represented at block 730 the rate is calculated as the rate sum multiplied by ⅝ which is the equivalent of two times the rate. Inasmuch as the rate queue is representative of one-half second in time, a resultant output from the instructions of block 730 provides a counts per second valuation.

Returning to FIG. 8B, upon calculation of the rate as described in conjunction with FIG. 13, and as represented at line 740, the program then updates the display 28 as represented by line 740 and block 742. Generally, such updating occurs about five times per second. Following the update as represented by line 744, the program considers the instructions of block 746. It may be observed that in the event a negative response occurs with respect to the inquiry at block 702, then the program proceeds as represented by line 748 and the noted line 744 to the instructions at block 746. Block 746 provides instructions to restore registers and terminate the program. Accordingly, as represented by line 750, the program returns to its start at line 352.

Since certain changes may be made in the above-described system, method and apparatus without departing from the scope of the invention herein involved, it is intended that all matter contained in the description thereof or shown in the accompanying drawings shall be interpreted as illustrative and not in a limiting sense.

We claim:

1. A system for detecting and locating sources of gamma radiation within a region of interest, comprising:
   a probe movable from position to position within said region of interest including:
   a housing having a forward portion extending to a radiation window positionable in the vicinity of a said source;
   detector means within said housing for deriving induced charges in response to gamma ray interaction therewith and providing corresponding output signals;
   transmission means for transmitting said output signals; and
   signal treatment means including:
   energy level network means for validating said output signals and deriving count signals in response thereto;
   control means responsive to said count signals for entering them into a continuously fed queue from earliest to latest received representing a given period of continuous sampling time, said control means effecting a select weighting of predetermined time defined increments of count signals within said queue and generating from said weighted count signals a stabilized count rate value; and
   perceptible indicator means for providing a perceptible output corresponding with said stabilized count rate value.

2. The system of claim 1 in which said queue receives said count signals to an extent representing a one-half second count time interval of twenty-five entries from said earliest to said latest.

3. The system of claim 2 in which the earliest increment of ten said entries is weighted by unity, the next latest increment of five entries is weighted by a factor of two, the next latest increment of five entries is weighted by a factor of four and the increment representing the five latest entries is weighted by a factor of eight.

4. The system of claim 3 in which said control means is responsive to sum said weighted twenty-five entries and multiply said sum by five eighths to derive said stabilized count rate value.

5. The system of claim 1 which:
   said perceptible indicator means provide an audible output in response to a drive signal of select frequency; and
   said control means includes memory means for retaining a sequence of frequency values representing a predetermined range of frequency signals from lowest to highest, and is responsive to said stabilized count rate value for accessing said memory means frequency values to generate said drive signal in correspondence therewith.

6. A system for detecting and locating gamma radiation source concentrations at specific tissue regions of an animal body further having a predetermined body region selectable as emanating gamma radiation at background levels, comprising:
   a probe movable from position to position along said tissue region and to said predetermined body region, including:
   a housing having a forward portion extending to a radiation window positionable in the vicinity of said tissue regions and said predetermined body region;
   detector means within said housing for deriving induced charges in response to gamma ray interaction therewith and providing corresponding output signals; and
   transmission means for transmitting said output signals; and
   signal treatment means including:
   energy level network means for validating said output signals and deriving count signals in response thereto;
   squelch mode activation means actuable for deriving a squelch range calibration sequence;
   audible indicator means for providing an audible output in response to input signals;
   memory means for retaining count rate data;
   control means responsive to said count signals derived when said probe is located at said predetermined body region for deriving a basic background count rate, responsive to said basic background count rate to derive a squelch low count rate, responsive to derive the product of said squelch low count rate and a predetermined range for deriving a squelch high count rate, responsive to retain said squelch low count rate and said squelch high count rate in said memory means, responsive subsequently to said count signals for deriving count rate signals, and for deriving said audible indicator input signals at predetermined frequencies corresponding therewith when said count rate signals exhibit a value intermediate said memory retained squelch low count rate and said squelch high count rate.

7. The system of claim 6 in which said signal treatment means control means is responsive to derive a squelch difference value as the difference between said squelch low count rate and said squelch high count rate, responsive to divide said squelch difference value by a predetermined rate limit time value to derive a squelch delta value, responsive to retain said squelch delta value in said memory means, and responsive to limit change of said audible indicator input signals to correspond with changes of said count rate signals of value at least equivalent to said memory means retained squelch delta value.

8. The system of claim 7 in which:
   said memory means includes a table of frequency deriving values representing lowest to highest said predetermined frequencies;
   said control means is responsive to current said count rate signals and previous said count rate signals to derive the difference therebetween as a rate delta value and responsive to effect access of a said memory means frequency deriving value in controlled correspondence to said current rate signals when the absolute value of said rate delta value equals or exceeds said squelch delta value.

9. The system of claim 8 in which said signal treatment means control means includes a system clock having a clock output of predetermined clock frequency, said memory means retained frequency deriving values are a sequence of values of system clock cycles, and said control means is responsive to select said frequency deriving values to provide interrupt signals as said input signals to said audible indicator means.

10. The system of claim 6 in which said signal treatment means control means is responsive to said squelch high count rate to derive a high rate limit of predetermined count rate value greater than said squelch high count rate, and is responsive to limit the value of said count rate signals to said high rate limit, so as to enhance response performance of said system.

11. The system of claim 6 in which said signal treatment means control means is responsive to said squelch low count rate to derive a low rate limit of predetermined count rate value less than said squelch low count rate, and is responsive to limit the minimum value of said count rate signals to said low rate limit, so as to enhance the response performance of said system.

12. The system of claim 6 in which:
   said signal treatment means control means is responsive to said squelch high count rate to derive a high rate limit of predetermined count rate value greater than said squelch high count rate, and is responsive to limit the value of said count rate signals to said high rate limit, so as to enhance response performance of said system; and
   said signal treatment means control means is responsive to said squelch low count rate to derive a low rate limit of predetermined count rate value less than said squelch low count rate, and is responsive to limit the minimum value of said count rate signals to said low rate limit, so as to enhance the response performances of said system.

13. The system of claim 6 in which said signal treatment means control means is responsive to derive said squelch low count rate as said basic background count rate combined with a reference deviation of said basic background count rate.

14. The system of claim 13 in which said reference deviation of said basic background count rate is twice the square root of said basic background count rate.

15. The system of claim 6 in which:
   said signal treatment means includes count mode activation means actuable for deriving a count rate mode when said probe is moved along said tissue regions; and
   said control means is responsive to said actuation of said squelch mode activation means and, subsequently, to said count mode activation means actuation to effect response to said count signals when said probe is located at said predetermined body region.

16. The system of claim 6 in which said control means is responsive to said count signals derived when said probe is located at said tissue regions for entering them into a continuously fed queue from earliest to latest received representing a given increment of continuous sampling time, said control means effecting a select weight of predetermined, time defined increments of count signals within said queue and generating said count rate signals from said weighted count signals as stabilized count rate values.

17. The system of claim 16 in which said queue receives said count signals to an extent representing a one-half second count time interval of twenty-five entries from said earliest to said latest.

18. The system of claim 17 in which the earliest increment of ten said entries is weighted by unity, the next latest increment of five entries is weighted by a factor of two, the next latest increment of five entries is weighted by a factor of four and the increment representing the five latest entries is weighted by a factor of eight.

19. The system of claim 18 in which said control means is responsive to sum and weighted twenty-five entries and multiply said sum by five eighths to derive said stabilized count rate value.

20. The method for generating audible cuing signals locating gamma radiation concentrations within tissue of an animal body, said body having a region selectable as emanating gamma radiation at background levels comprising the steps of:
providing a hand manipular probe movable about said tissue and generating output signals in response to gamma radiation impinging thereon;
positioning said probe at said body region and evaluating said output signals for a predetermined interval to derive a squelch low background count rate;
deriving a squelch high count rate by multiplying said squelch low background count rate by a select range factor;
deriving a squelch difference value as the difference between squelch low background count rate and said squelch high count rate;
deriving a squelch delta value by dividing said squelch difference value by a predetermined time value;
providing a memory retained table of frequency deriving values from lowest to highest;
providing an audible sound generator actuable to produce a cuing sound output at frequencies of value selected from said table of frequency values;
positioning said probe at select locations of said tissue of said animal body and determining previous and next count rates from resulting said output signals;
accessing said table of frequency deriving values in correspondence with said previous count rate as a proportion of said squelch difference to provide a first said frequency deriving value;
actuating said sound generator in correspondence with said first frequency deriving value;
determining a rate delta value as the difference between said previous and next count rates;
comparing said rate delta value with said squelch delta value and accessing said table of frequency values in correspondence with a frequency value representing the sum of said previous count rate and said squelch delta value as a proportion of said squelch difference when said rate delta value equals or exceeds said squelch delta value to determine a second said frequency deriving value;
accessing said table of frequency deriving values for said second frequency deriving value; and
actuating said sound generator in correspondence with said second frequency deriving value.

21. The method of claim 20 wherein said sound generator is actuated in correspondence with said first frequency when said rate delta value is less than said squelch delta value.

22. The method of claim 20 in which said squelch low background count rate is derived as the count rate of said output signals summed with the value of a reference deviation thereof.

23. The method of claim 20 in which said previous and next count rates are determined by selectively weighting predetermined time defined increments of said output signals.

24. The method of claim 20 in which said range factor is selected as about 1.5.

* * * * *